United States Patent
Wang et al.

(10) Patent No.: US 8,194,820 B2
(45) Date of Patent: Jun. 5, 2012

(54) OPTIMAL WEIGHTS FOR MEASURING SPECTRAL X-RAY DATA

(75) Inventors: Adam S. Wang, Stanford, CA (US); Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 277 days.

(21) Appl. No.: 12/700,558

(22) Filed: Feb. 4, 2010

(65) Prior Publication Data

US 2010/0202584 A1     Aug. 12, 2010

Related U.S. Application Data

(60) Provisional application No. 61/150,635, filed on Feb. 6, 2009.

(51) Int. Cl.
*G01N 23/06* (2006.01)
*H05G 1/64* (2006.01)

(52) U.S. Cl. ........................................ 378/53; 378/98.9

(58) Field of Classification Search .................... 378/53, 378/54, 57, 62, 98.9, 98, 98.11, 98.12
See application file for complete search history.

(56) References Cited

U.S. PATENT DOCUMENTS

| 4,029,963 | A | | 6/1977 | Alvarez et al. |
| 6,018,562 | A | * | 1/2000 | Willson ............................ 378/9 |
| 6,597,758 | B1 | * | 7/2003 | Rosner ............................ 378/53 |
| 2002/0094062 | A1 | * | 7/2002 | Dolazza et al. .............. 378/98.9 |
| 2006/0067461 | A1 | * | 3/2006 | Yin et al. ............................ 378/5 |

OTHER PUBLICATIONS

A. S. Wang and N. J. Pelc, "Optimal Energy Thresholds and Weights for Separating Materials Using Photon Counting X-Ray Detectors with Energy Discriminating Capabilities," Medical Imaging 2009: Physics of Medical Imaging, Proceedings of SPIE, vol. 7258, No. 725821 (2009).
Wang et al., "Sufficient Statistics as a Generalization of Binning in Spectral X-Ray Imaging," IEEE Trans Med Imaging, vol. 30(1), pp. 84-93, Jan. 2011, Epub. Aug. 3, 2010.

* cited by examiner

*Primary Examiner* — Irakli Kiknadze
(74) *Attorney, Agent, or Firm* — Beyer Law Group LLP

(57) ABSTRACT

A method for determining a composition of an object using a spectral x-ray system is provided. X-ray photons of at least two different energies are transmitted through the object. The energy of each detected x-ray photon using a detector in the x-ray system is estimated. A first weighted sum of the number of detected photons of each energy is found using a first weighting function, wherein the first weighting function is dependent on the attenuation coefficient function of a first material. In another embodiment, the photons are binned into two energy bins wherein there is a gap between the energy bins.

18 Claims, 21 Drawing Sheets

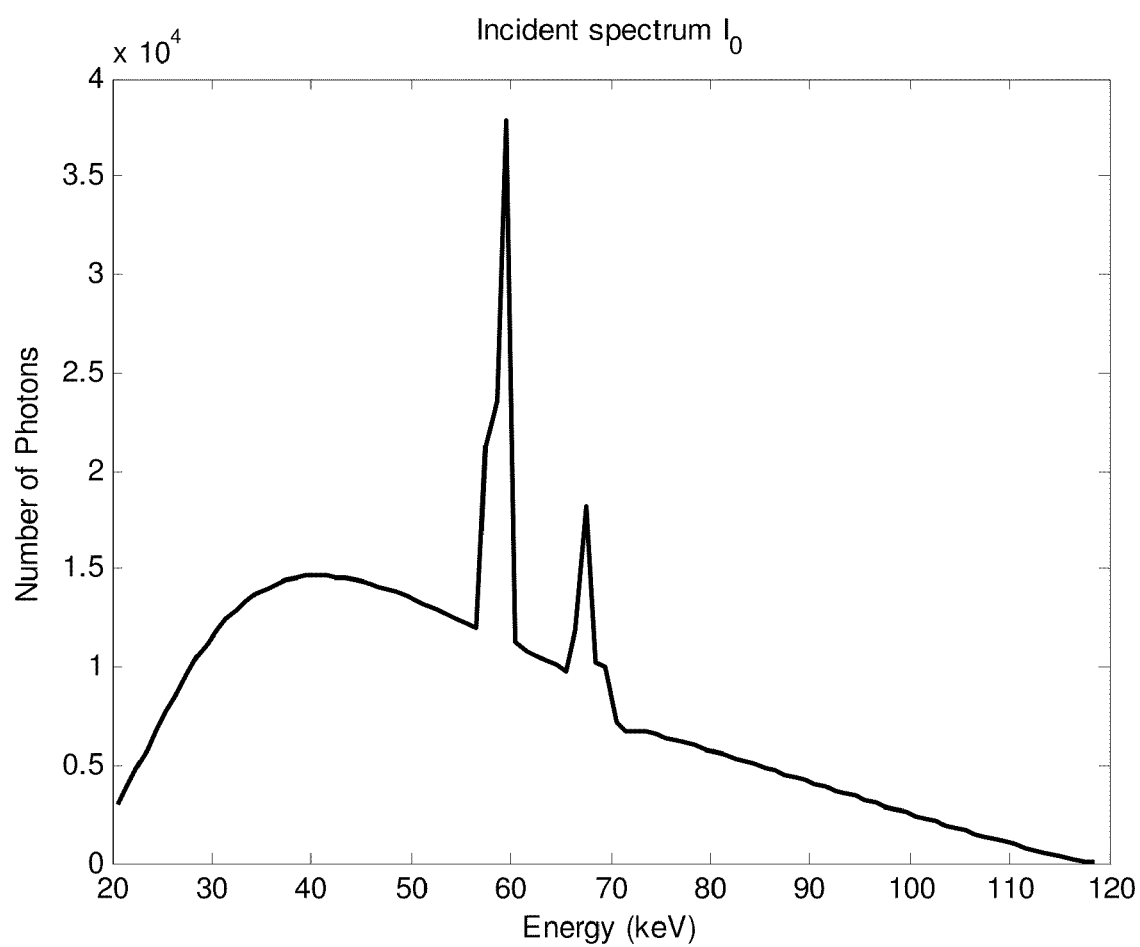
FIG. 2b Incident Spectrum

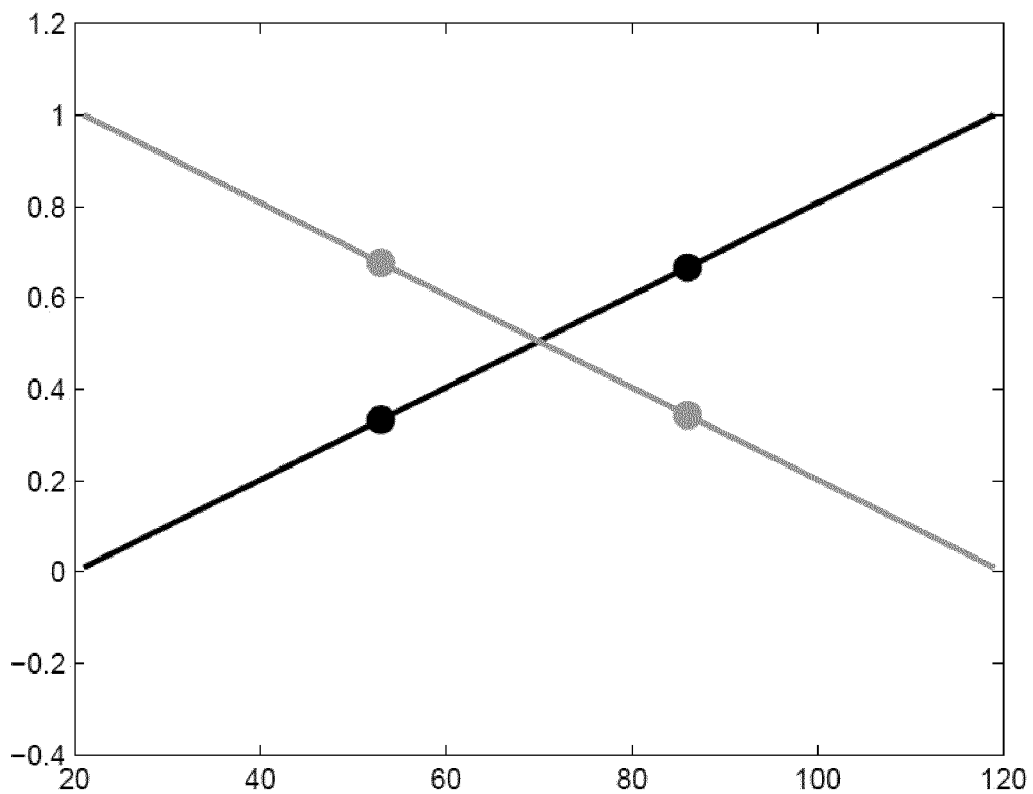
FIG. 5a Initial Weights
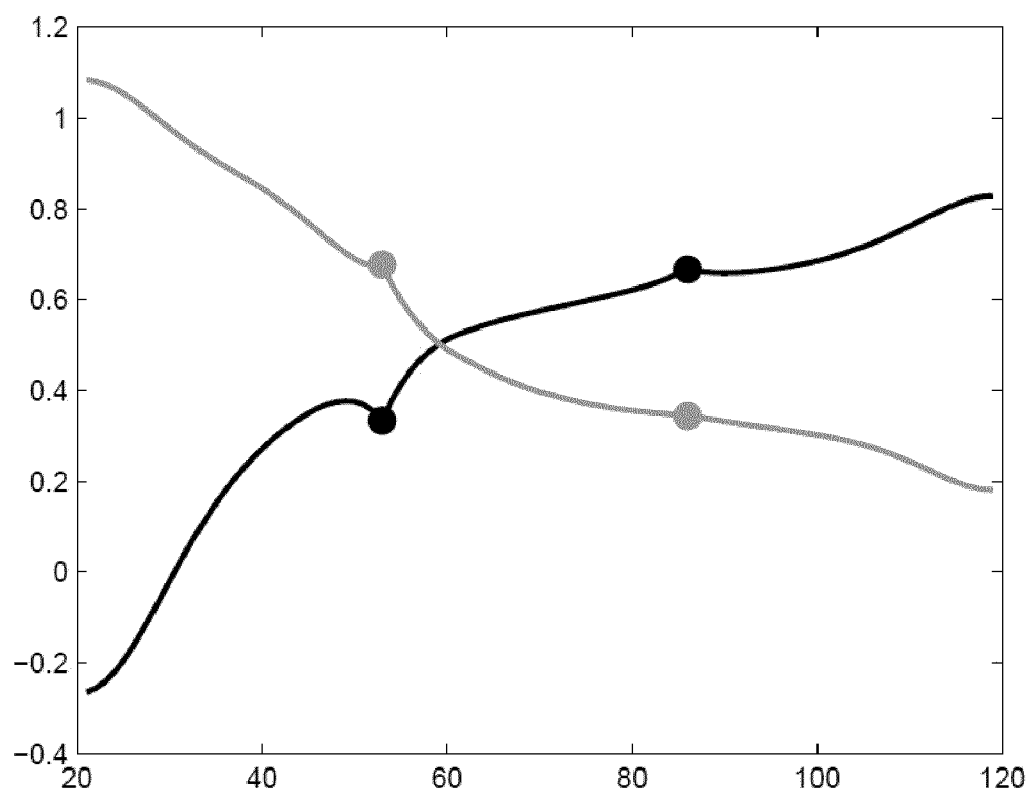
FIG. 5b Iteration 100

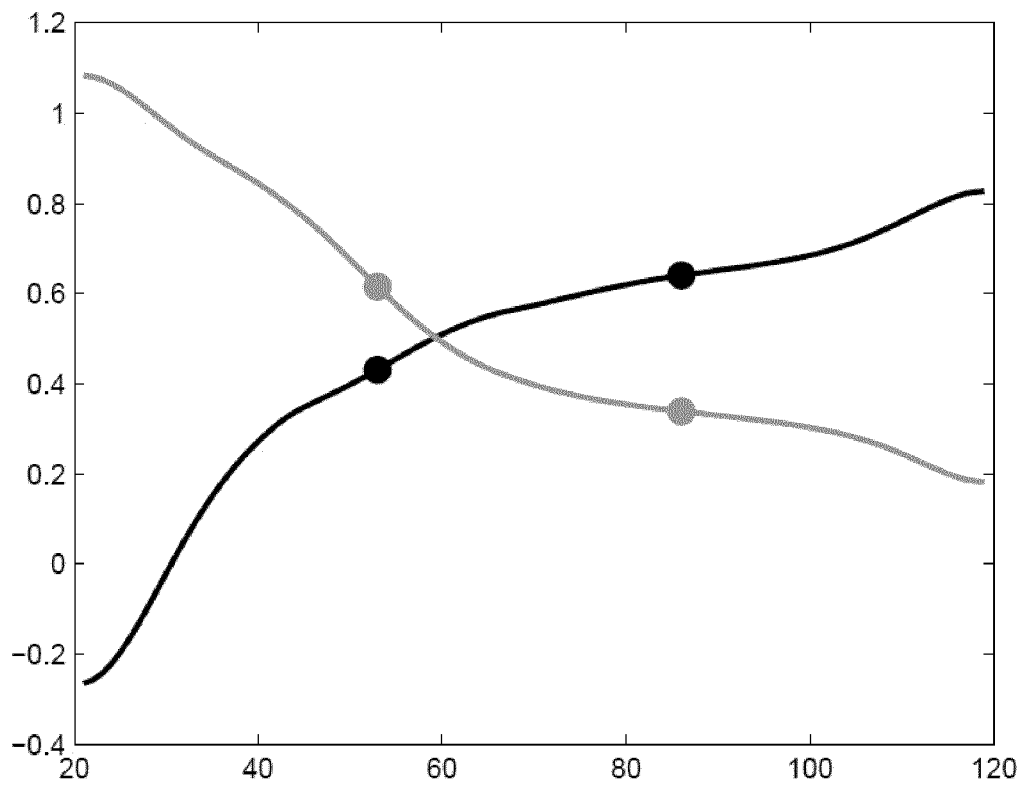
FIG. 5c Iteration 101
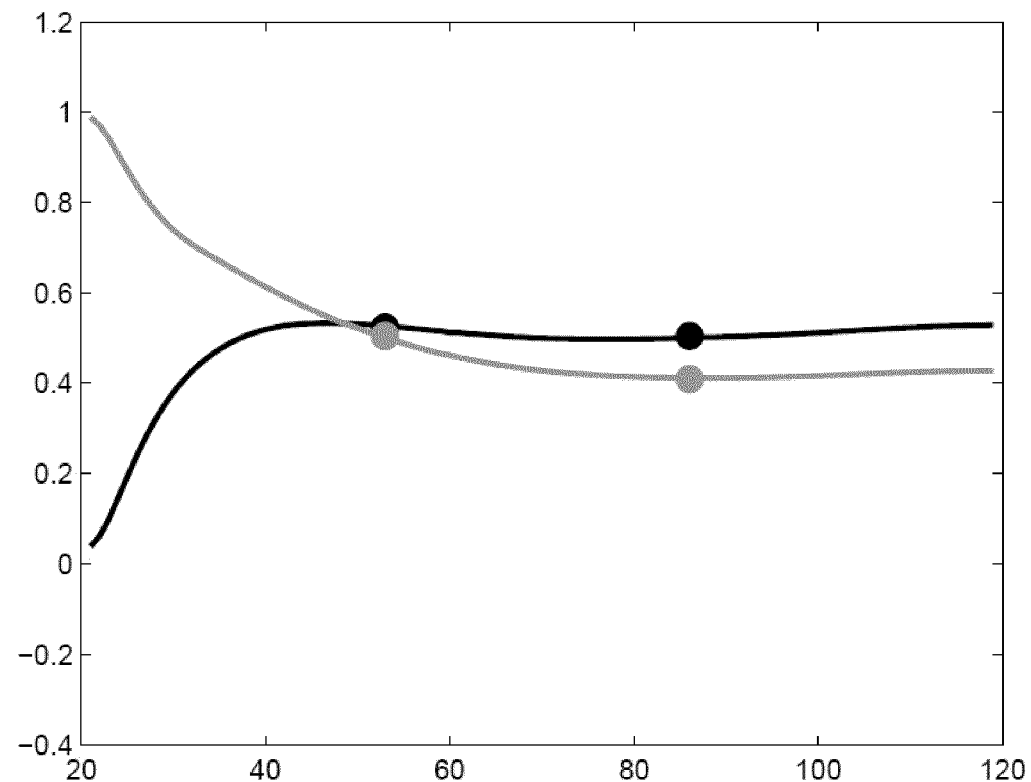
FIG. 5d Iteration 626

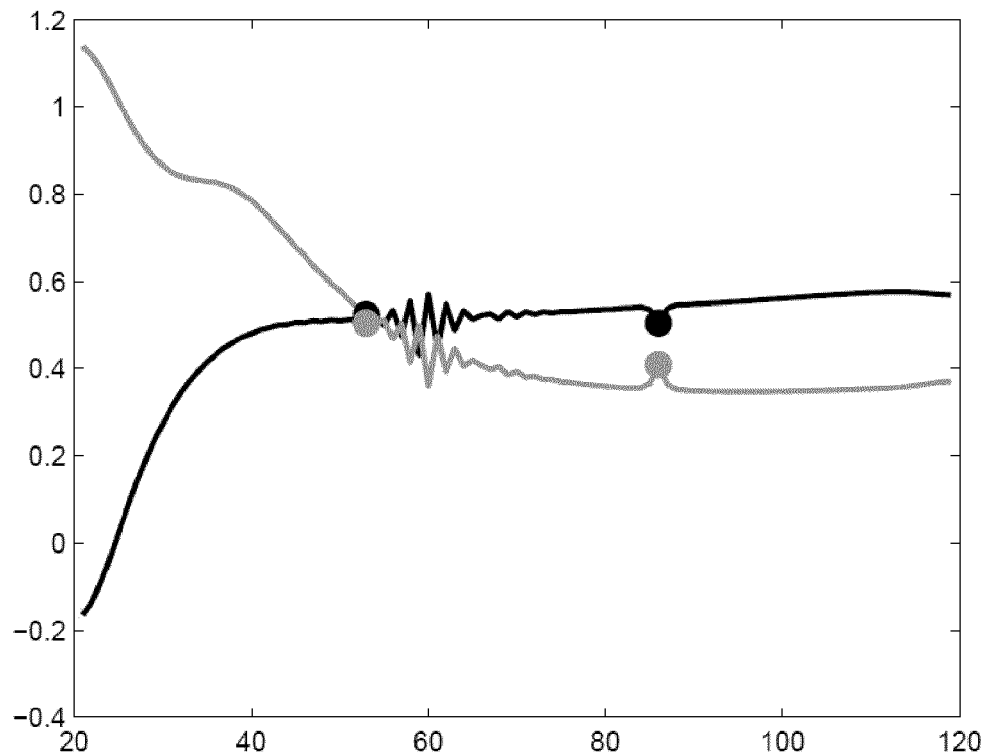
FIG. 5e Iteration 700
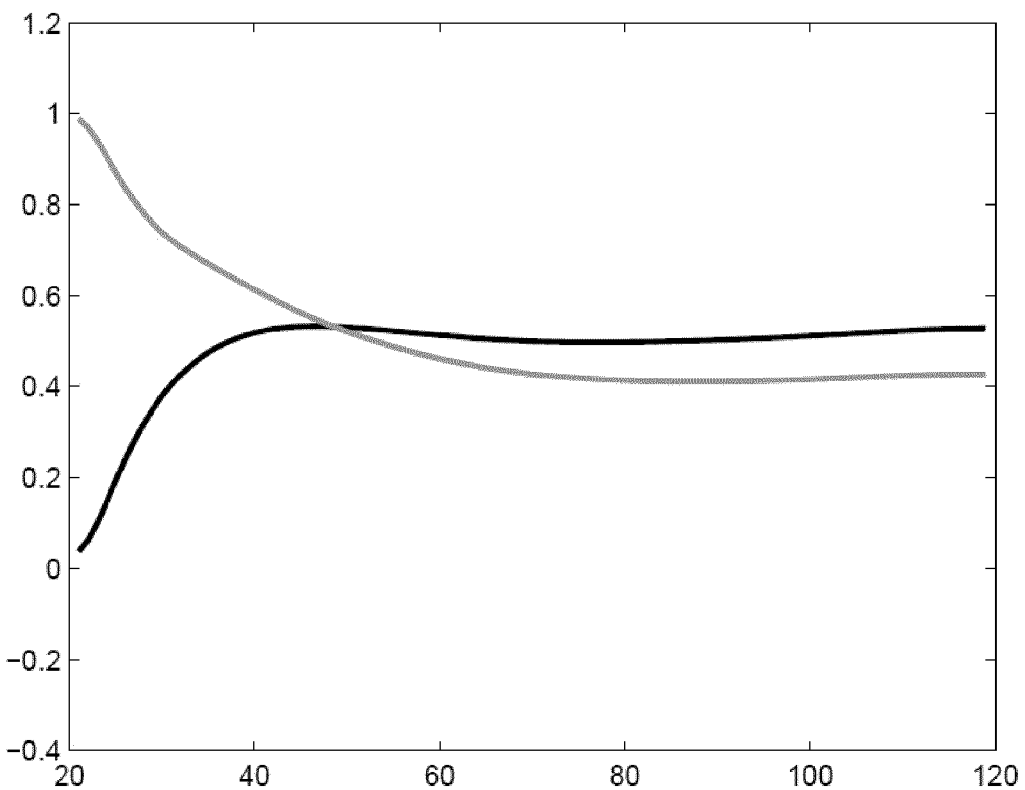
FIG. 5f Optimal Weights

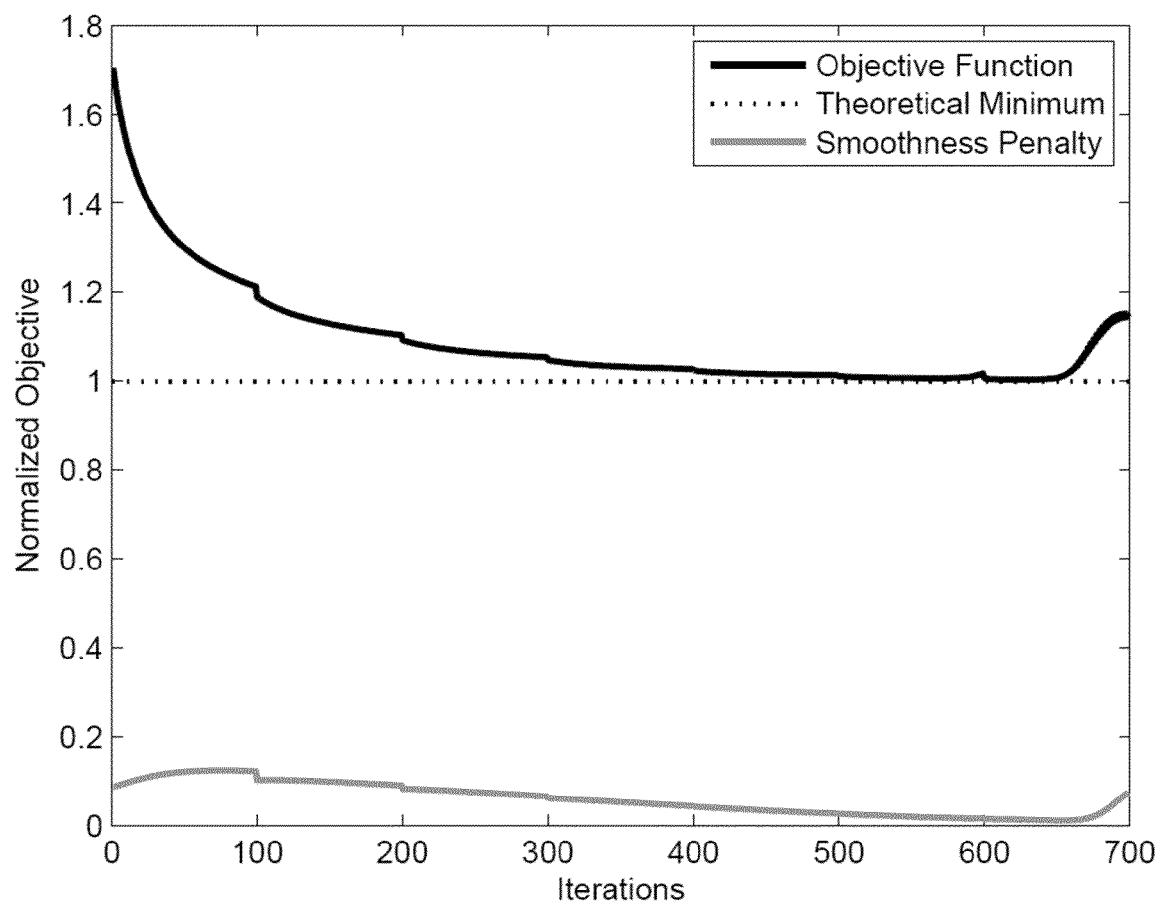
FIG. 5g Objective Function

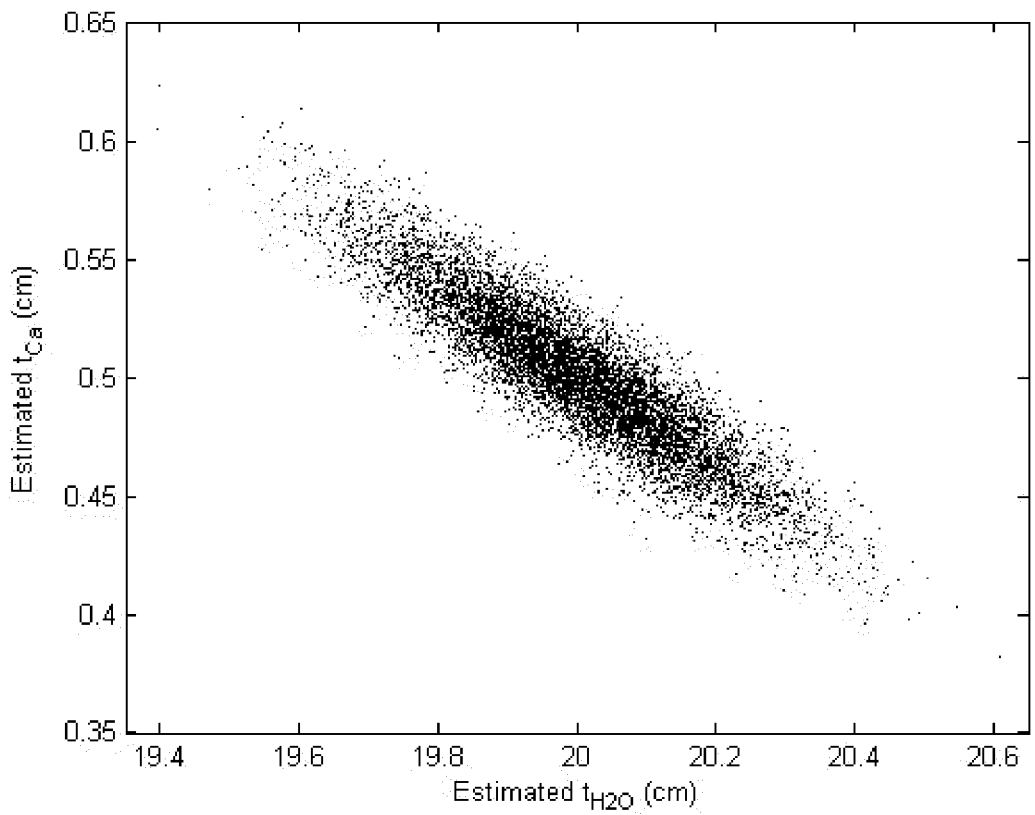
FIG. 6a Optimal Weights
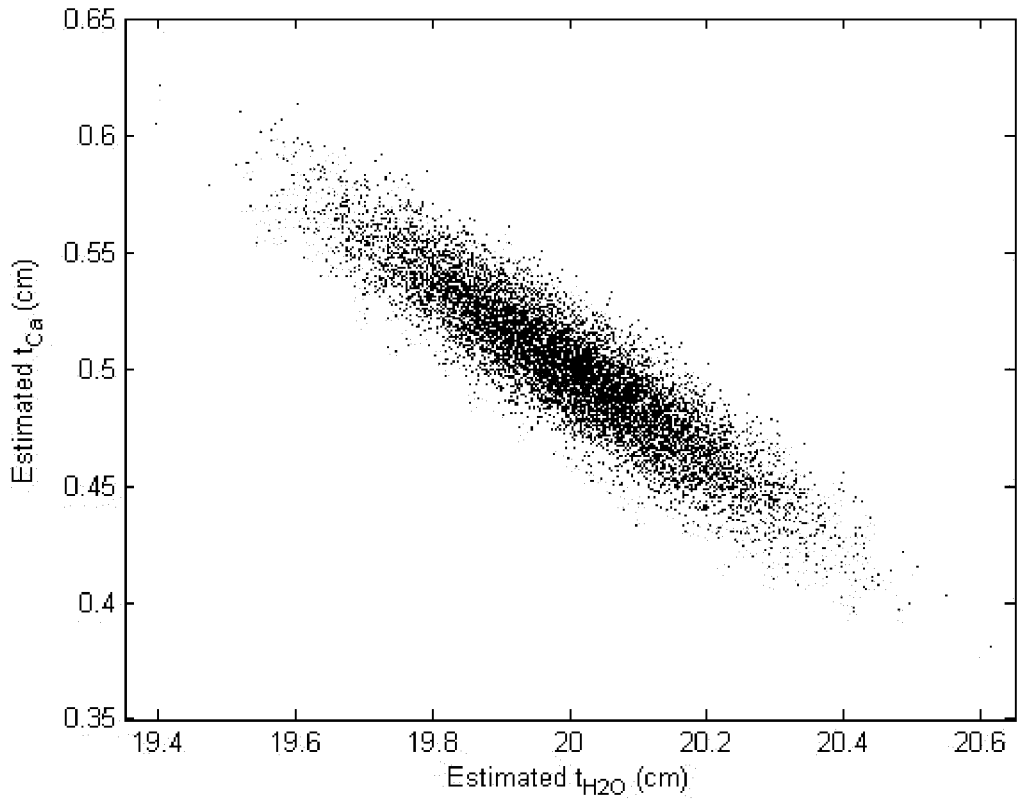
FIG. 6b Ideal keV bins

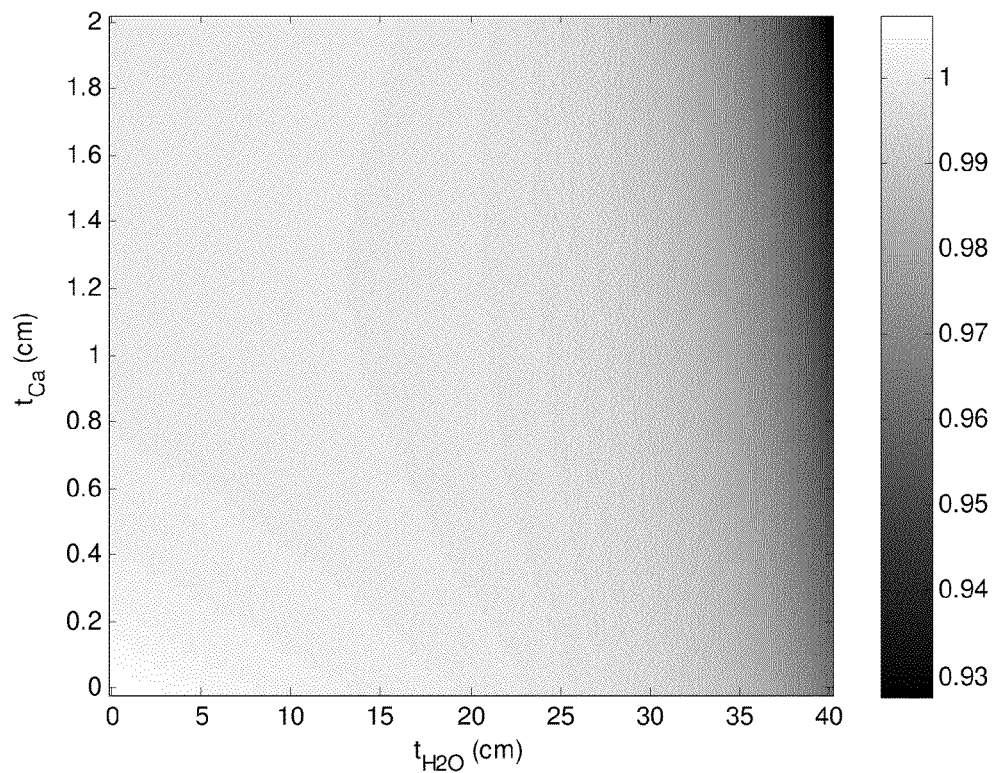
FIG. 7a Normalized $\mathrm{Var}(\hat{t}_{Ca})$
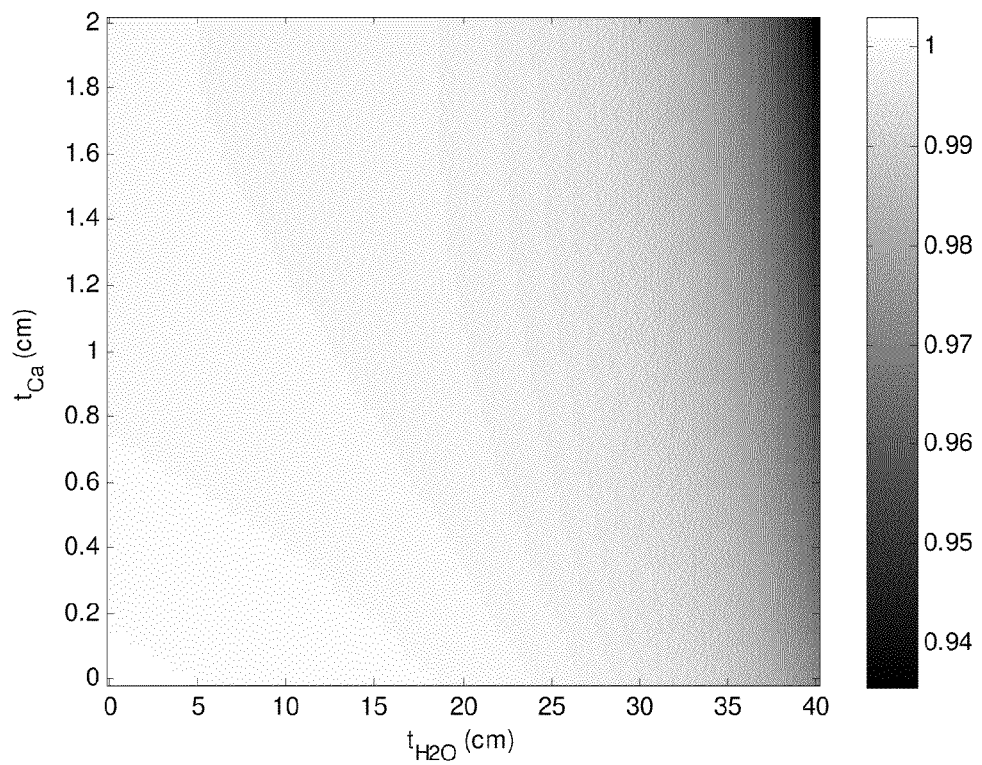
FIG. 7b Normalized $\mathrm{Var}(\hat{t}_{H_2O})$

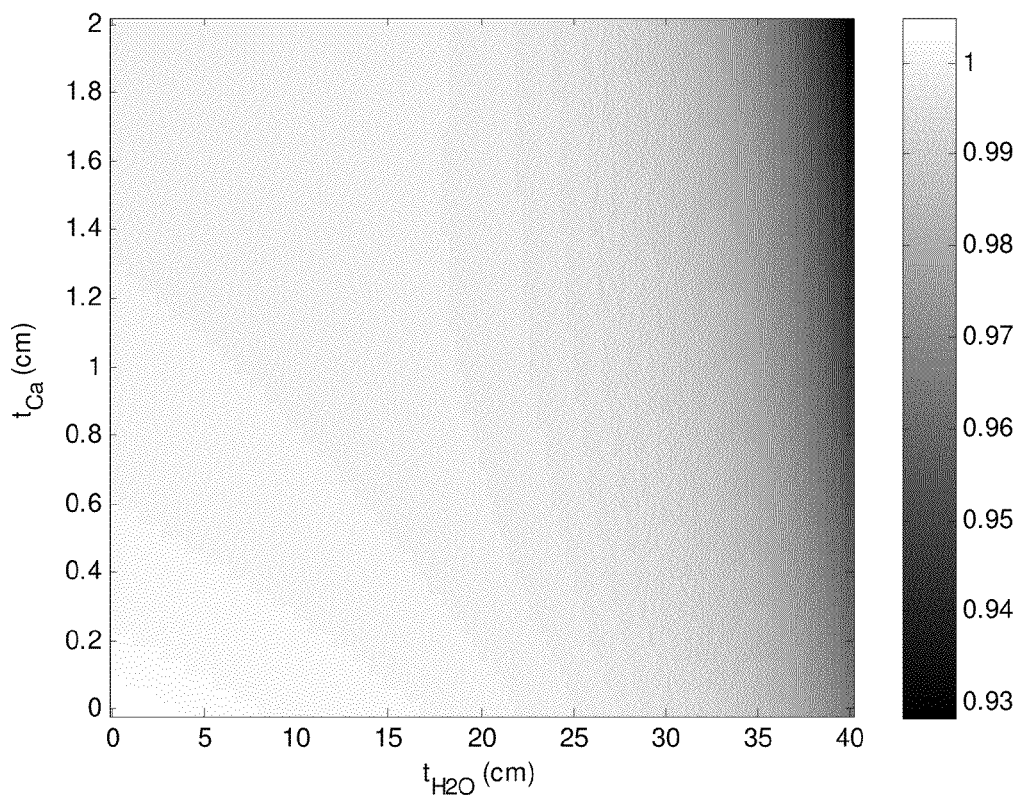
FIG. 7c Normalized $\mathrm{Cov}(\hat{t}_{Ca}, \hat{t}_{H_2O})$
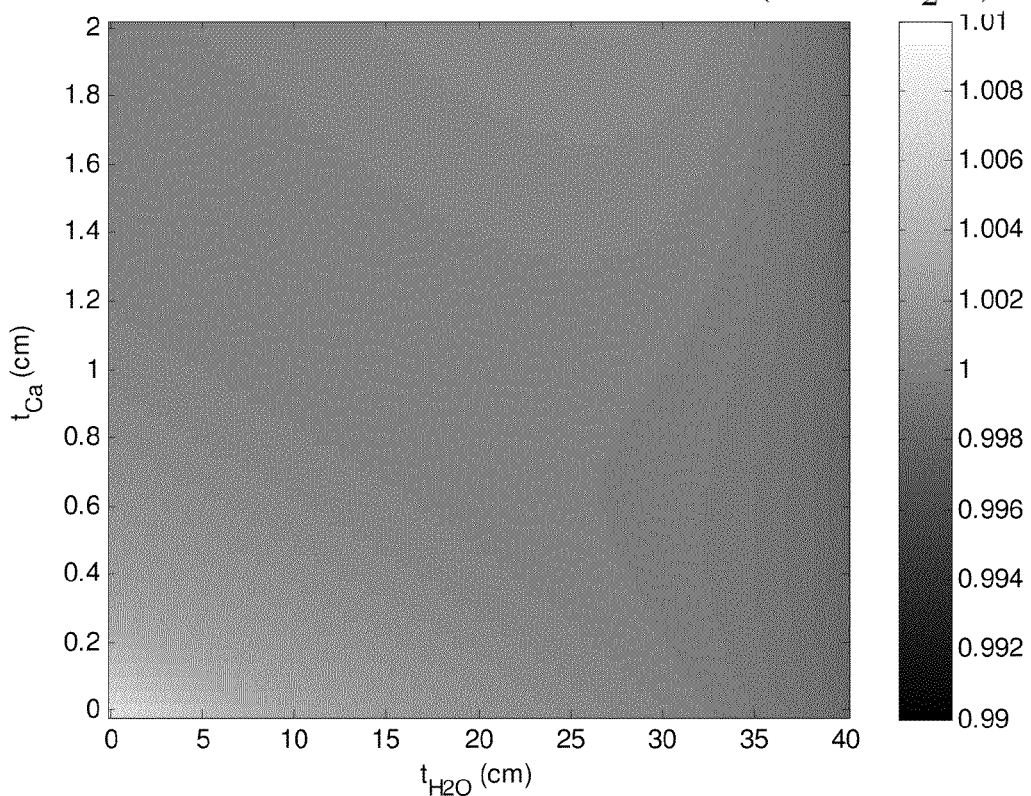
FIG. 7d Normalized $\mathrm{Var}(\hat{t}_{Ca})$, $I'_0 = 20 I_0$

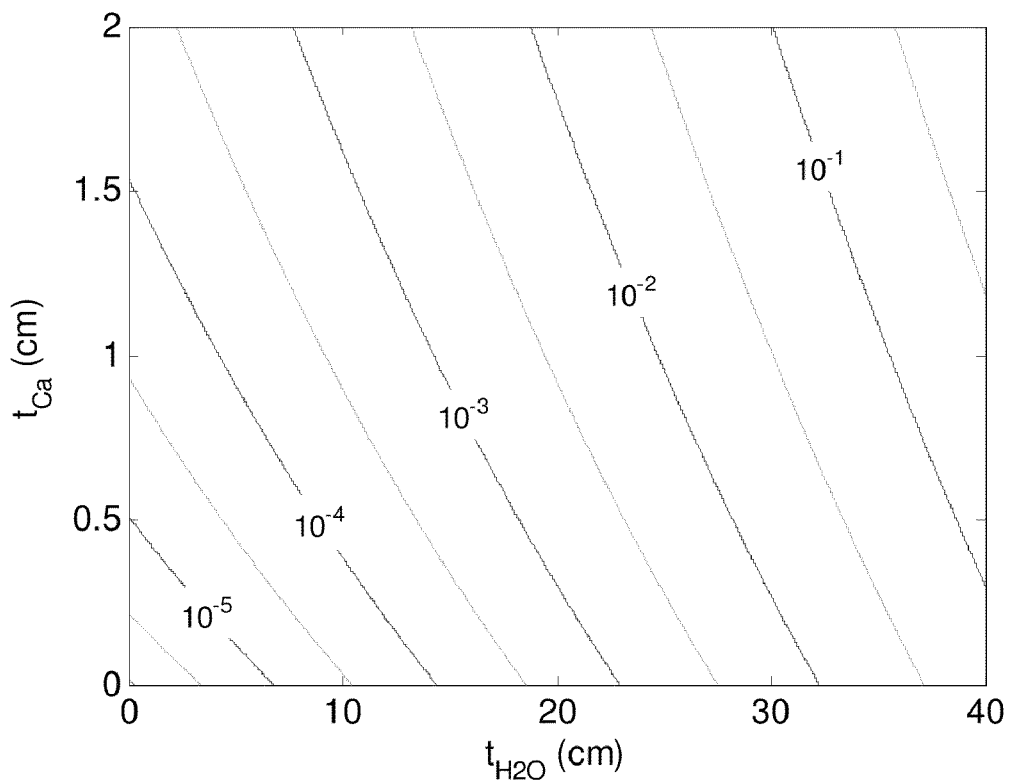
FIG. 10a $\mathrm{Var}(\hat{t}_{Ca})$: Full spectrum
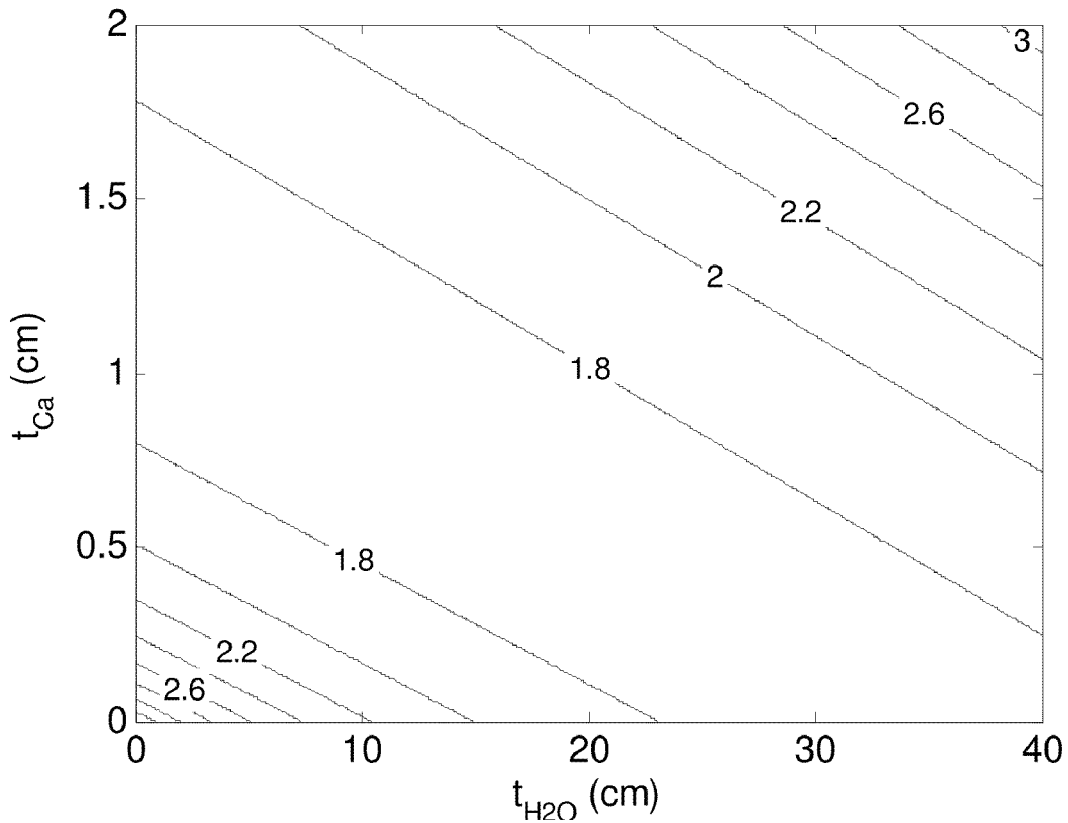
FIG. 10b $\mathrm{Var}(\hat{t}_{Ca})$ penalty: 2 bins, 57 keV

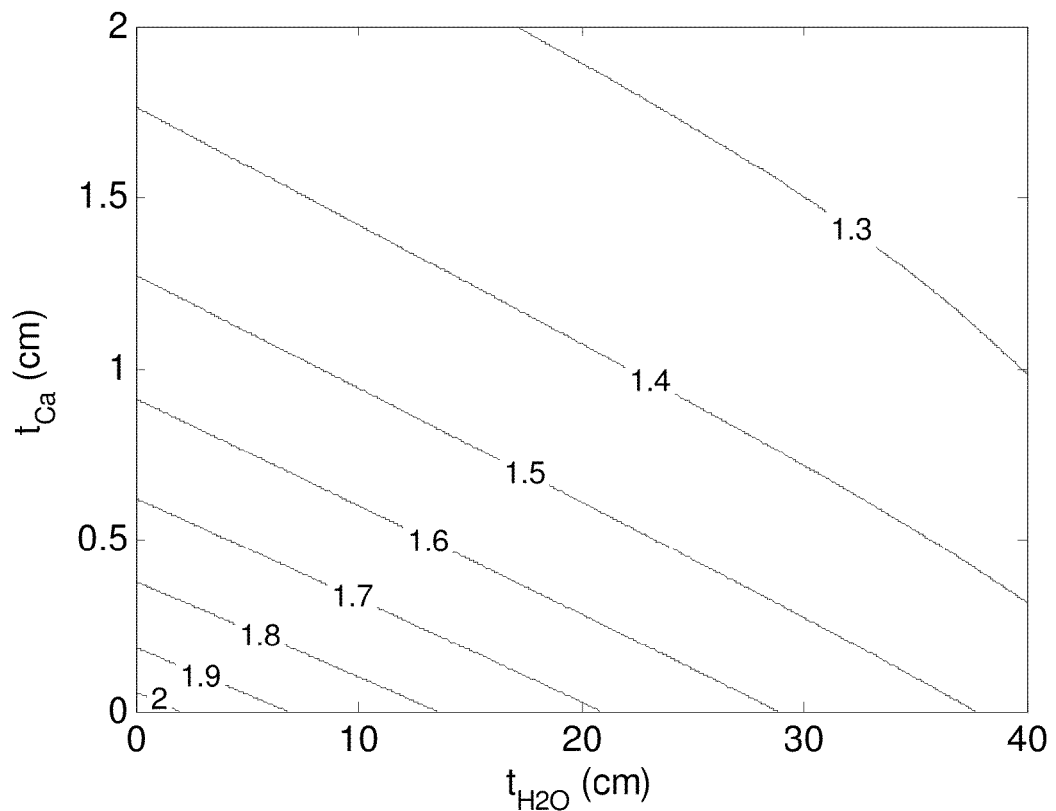
FIG. 10c $\mathrm{Var}(\hat{t}_{\mathrm{Ca}})$ penalty: CIX
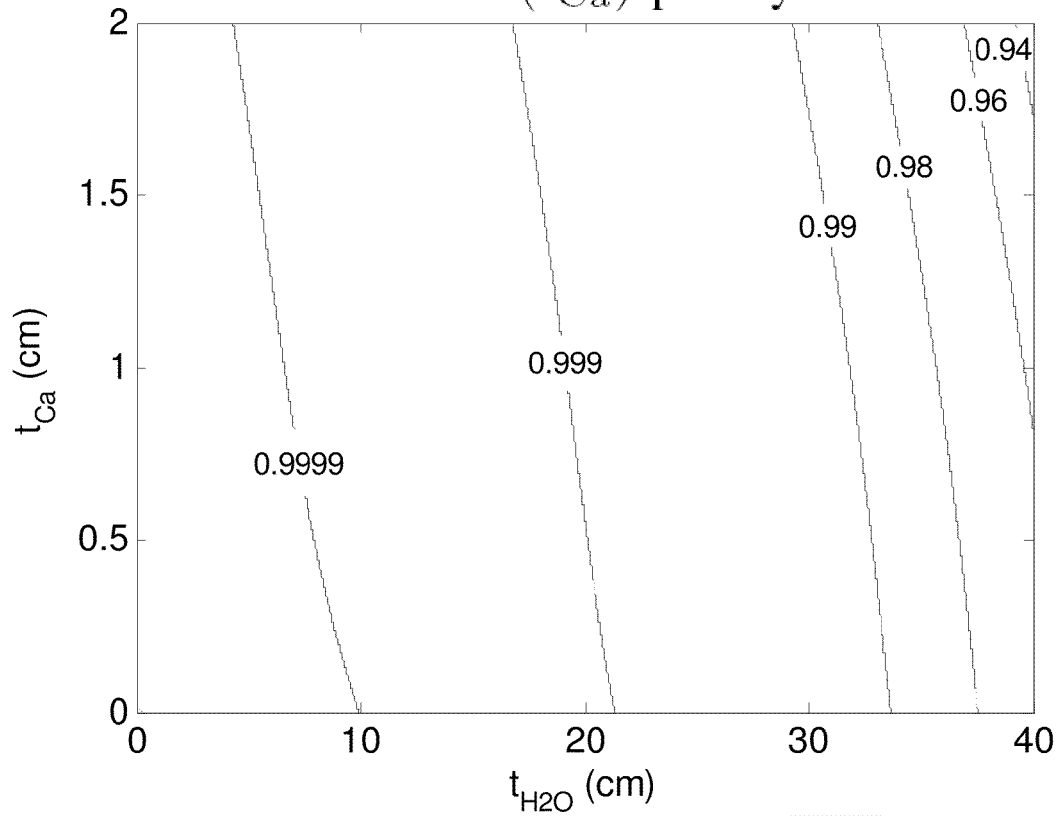
FIG. 10d $\mathrm{Var}(\hat{t}_{\mathrm{Ca}})$ penalty: $\mu$-weights, Gaussian

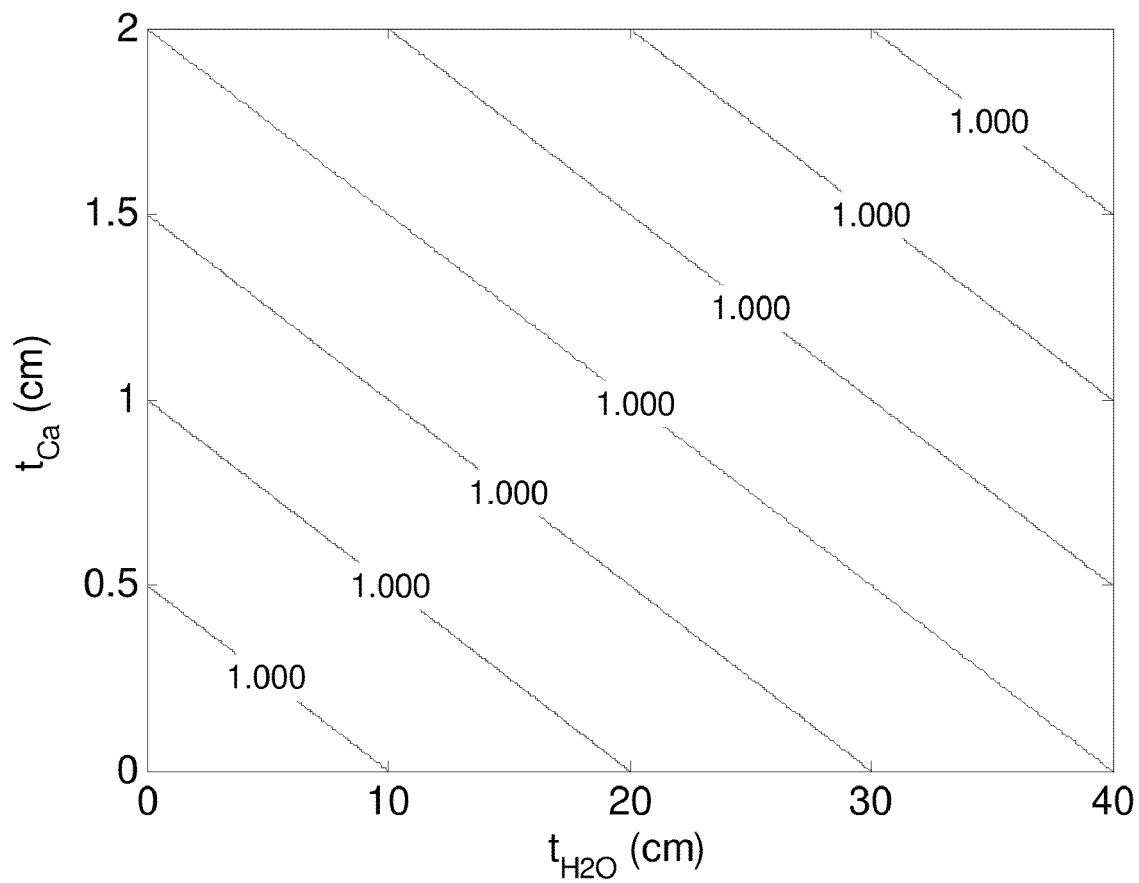
FIG. 10e $\mathrm{Var}(\hat{t}_{\mathrm{Ca}})$ penalty: $\mu$-weights, Exact
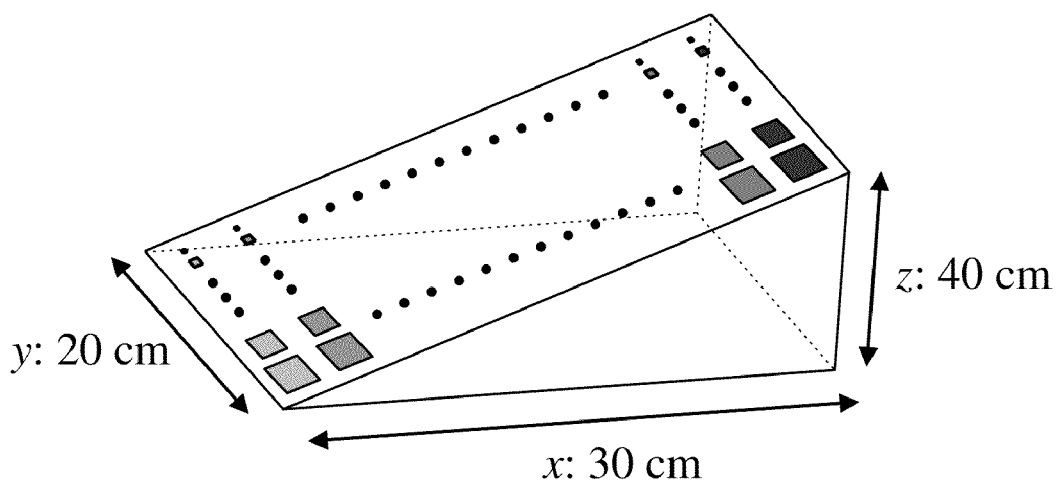
FIG. 11a Wedge Phantom

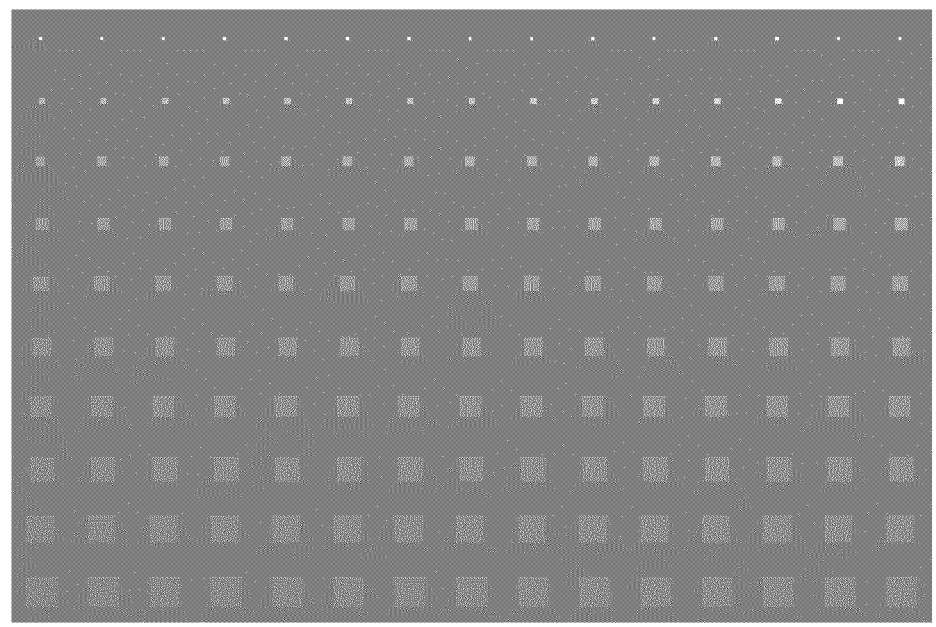
FIG. 11b True $t_{Ca}$
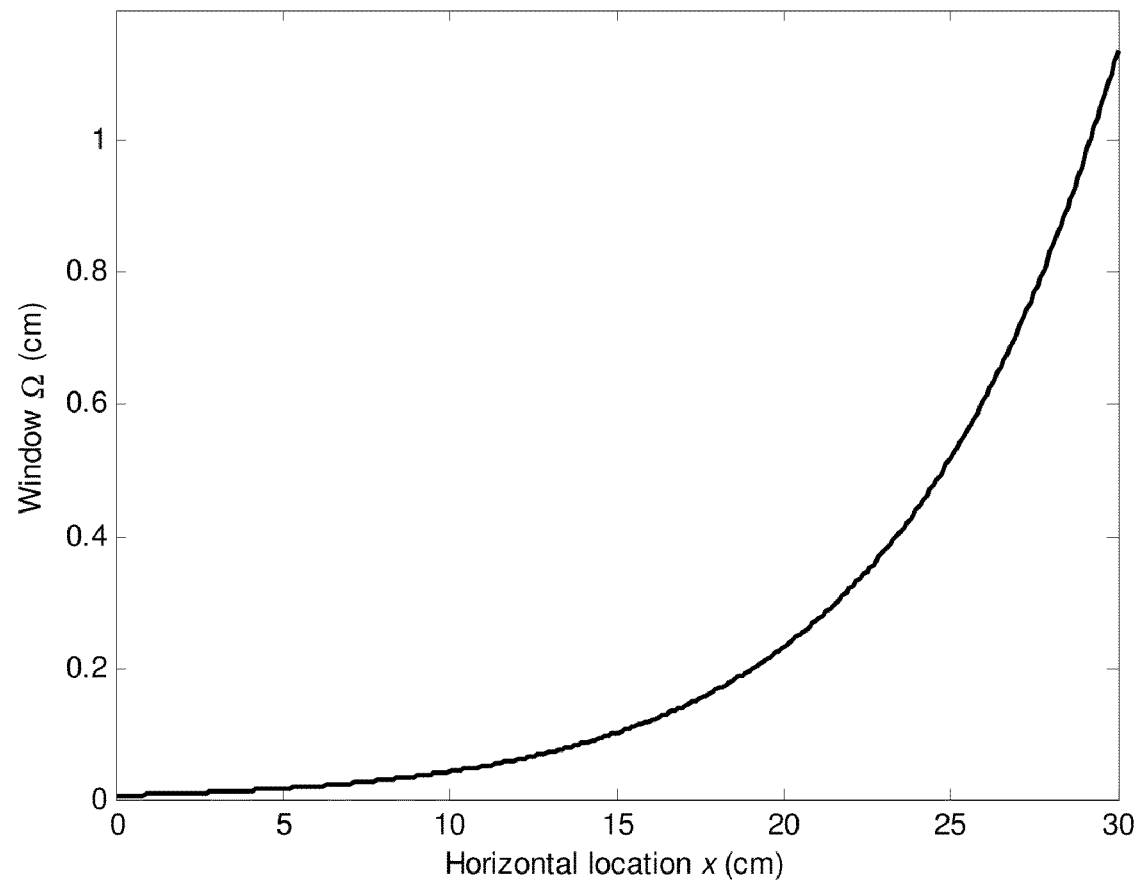
FIG. 11c Spatially varying $\Omega$

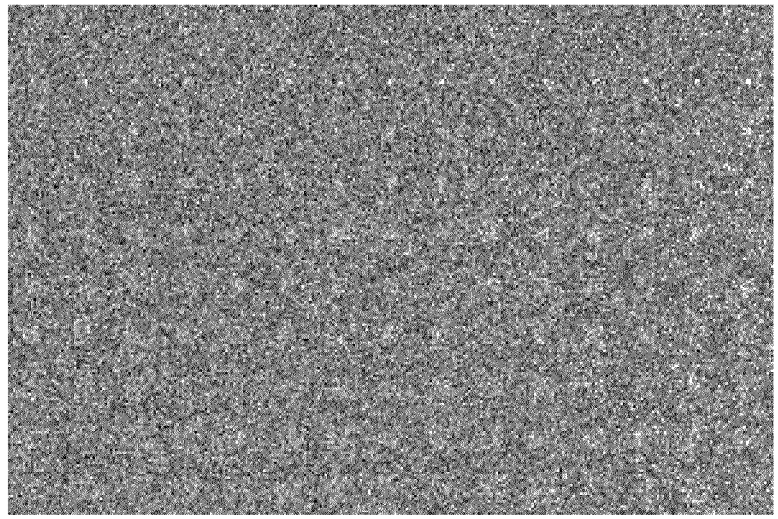
FIG. 11d $\hat{t}_{Ca}$: 2 bins, 57.5 keV threshold
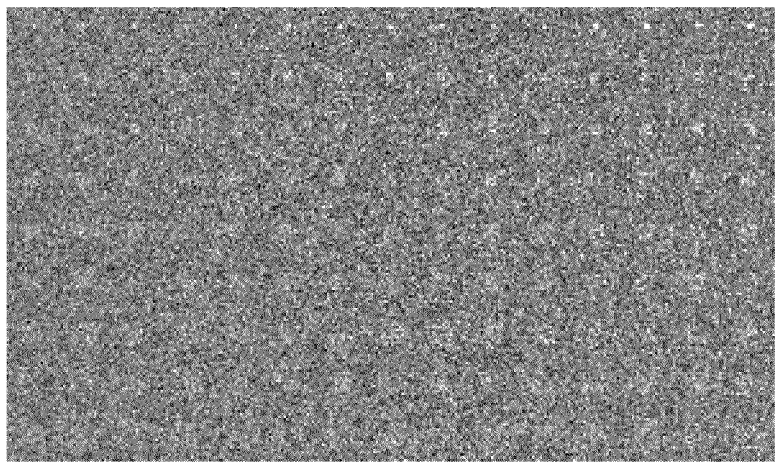
FIG. 11e $\hat{t}_{Ca}$: CIX
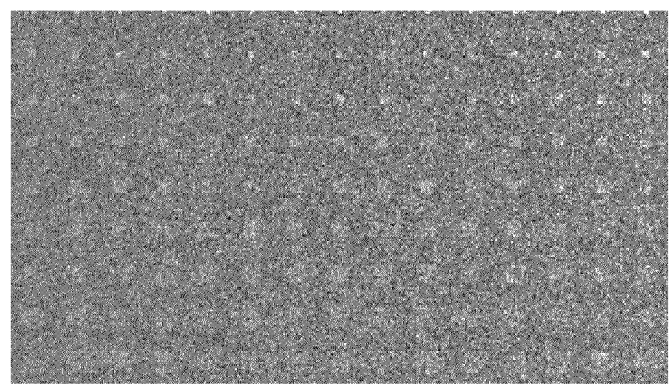
FIG. 11f $\hat{t}_{Ca}$: $\mu$-weights

OPTIMAL WEIGHTS FOR MEASURING SPECTRAL X-RAY DATA

CROSS REFERENCE TO RELATED APPLICATIONS

This application claims priority under 35 U.S.C. §119(e) from co-pending U.S. Provisional Application No. 61/150,635, entitled "OPTIMAL WEIGHTS FOR MEASURING SPECTRAL X-RAY DATA", filed Feb. 6, 2009, and naming Wang et al. as inventors, which is incorporated by reference in its entirety for all purposes.

BACKGROUND OF THE INVENTION

This invention relates generally to x-ray imaging including computed tomography (CT). More specifically the invention relates to a spectral x-ray imaging.

Decomposing an object into attenuation or material basis functions provides additional imaging benefits such as contrast enhancement or material subtraction. This can be accomplished with photon counting x-ray detectors (PCXDs) with energy discriminating capabilities, which enable us to count x-ray photons and classify them based on their energies. The richness of the information contained in these measurements can depend heavily on how the information about the detected photons is collected.

SUMMARY OF THE INVENTION

In accordance with the invention, a method for determining a composition of an object using a spectral x-ray system is provided. X-ray photons of at least two different energies are transmitted through the object. The energy of each detected x-ray photon is estimated using a detector in the x-ray system. A first weighted sum of the number of detected photons of each energy is found using a first weighting function, wherein the first weighting function is dependent on the attenuation coefficient function of a first material.

In another manifestation of the invention, a method for determining a composition of an object using a spectral x-ray system is provided. X-ray photons of at least two different energies are transmitted through the object. The energy of each detected x-ray photon is estimated using a detector in the x-ray system. Each detected x-ray photon is binned according to energy in at least two bins, wherein a gap is between energy thresholds between two bins, wherein photons with energies corresponding to the gap are not counted in any bin.

In another manifestation of the invention, an apparatus for determining a composition of an object using a spectral x-ray system is provided. A spectral x-ray source for providing x-ray photons of at least two different energies is placed on a first side of the object. A detector for detecting and estimating energies of detected photons is placed on a second side of the object. A controller is controllably connected to the spectral x-ray source and the detector, and comprises at least one processor and computer readable media. The computer readable media comprises computer readable code for transmitting x-ray photons of at least two different energies through the object, computer readable code for estimating the energy of each detected x-ray photon using a detector in the x-ray system, and computer readable code for finding a first weighted sum of the number of detected photons of each energy using a first weighting function, wherein the first weighting function is dependent on the attenuation coefficient function of a first material.

The invention, objects and features thereof will be more readily apparent from the following detailed description and appended claims when taken with the drawings.

BRIEF DESCRIPTION OF THE DRAWINGS

FIG. 2b shows an incident spectrum.

FIG. 5a-g are graphs of the weights and an objective function.

FIG. 6a-b show resulting MLE estimates of t.

FIG. 7a-d are graphs of the performance of optimal weights as a function of t.

FIG. 10a-e are graphs of the CRLB performance for different weighing schemes, with different contour levels in the subfigures.

FIG. 11a-f show this wedge phantom, a true $t_{Ca}$ graph, a window $\Omega$ versus horizontal location graph and common thickness estimations with different weighing schemes, displayed on varying grayscale range $[-\Omega(x)+\Omega(x)]$.

DETAILED DESCRIPTION OF ILLUSTRATED EMBODIMENTS

Figure 1:
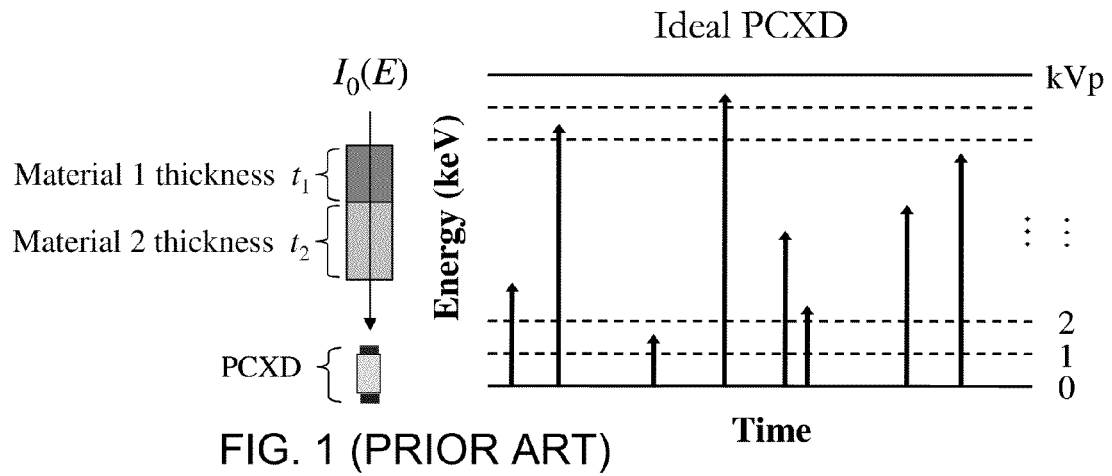
FIG. 1 is a schematic illustration in which a PCXD sorts and counts photons by their energy, where each impulse on the right represents the energy of a detected photon, which is counted in an appropriate bin by an idealized detector.

Embodiments of the invention provide methods that yield the optimal energy thresholds and/or weights for binning data from energy discriminating (photon counting x-ray directors) PCXDs. Additional energy information from these PCXDs allows us to use an estimator such as maximum-likelihood to estimate the amount of the basis materials penetrated by the beam. However, due to inherent quantum noise, these estimates are themselves noisy. We show that for PCXDs that discriminate between low and high energy photons, it is beneficial to have a gap between the thresholds. Photons with energies that fall into this gap should either be discarded or counted separately to improve material separability. Furthermore, if the PCXD can discern the energy of each photon, we show that when estimating the amount of each of two material basis functions, two appropriately weighted sums of the photon counts provide as much information as knowing the number of counts at each energy.

Advances in CT source and detector technologies have brought back much attention to dual- and multi-energy imaging. While there are advantages and disadvantages to each of the many spectral imaging techniques, PCXDs with energy discriminating capabilities ideally allow us to extract as much information as possible from the photons that are transmitted through the scanned object. These advanced detectors have the capability of providing more information than the same scan acquired with traditional energy integrating detectors since the energy of each photon can be discerned. However, their full potential in reducing noise or separating materials depends on how information is measured, combined, and extracted. Therefore, our goal is to identify methods that yield the optimal energy thresholds and/or weights for binning photons.

Like many dual-energy tasks, we are interested in estimating the unknown amounts of two known materials. We use a known incident polychromatic x-ray spectrum whose transmission through the object is measured by a PCXD with energy discriminating capabilities. Even if the composition of the object is unknown, our analysis holds under the weaker assumption that attenuation as a function of x-ray energy is a property of two mechanisms, or basis functions: photoelectric and Compton. While the traditional view of PCXDs is that they distribute photon counts into two or more energy bins based on simple thresholds, we will generalize the notion of ideal PCXDs to several forms. For each form, we first construct the theory behind evaluating the performance of an estimator that uses the measured data, and then optimize the detector parameters for a specific example.

II. Model

Consider an incident x-ray spectrum $I_0(E)$ with maximum energy M and attenuation basis functions $\mu_1(E)$ and $\mu_2(E)$ that are functions of x-ray energy E. In this application, we consider energies to the nearest keV. For an ideal detector with 1 keV resolution, the expected number of photons of energy j that fall on the detector is $\lambda_j = I_{0,j}\exp(-(t_1\mu_{1,j} + t_2\mu_{2,j}))$ where $I_{0,j} = I_0(j), \mu_{1,j} = \mu_1(j), \mu_{2,j} = \mu_2(j)$, and $t_1$ and $t_2$ are the thicknesses of material 1 and 2, respectively. If we consider quantum statistics, then the number of photons of energy j that fall on the detector, $r_j$, is a Poisson distribution with mean $\lambda_j$; that is $r_j \sim \text{Poisson}(\lambda_j)$.

FIG. 1 is a schematic illustration in which a PCXD sorts and counts photons by their energy, where each impulse on the right represents the energy of a detected photon, which is counted in an appropriate bin by an idealized detector. Suppose that for each photon counted, the detector can increment the count in one of N bins, as shown in FIG. 1. For instance, if there are 2 bins, then the detector could increment the count in a "low energy" bin or a "high energy" bin depending on whether an incident photon is below or above some cutoff threshold energy. Therefore, $d_i$, the number of detected counts in bin i is given by:

$$d_i = \sum_{j=\tau_{i-1}+1}^{\tau_i} r_j,$$

for i=1, . . . , N, and where $\{\tau_i\}$ are the cutoff threshold energies, with $\tau_0 = 0$ and $\tau_N = M$.

Because $d_i$ is a sum of Poisson random variables, $d_i$ is itself a Poisson random variable with mean $$\gamma_i = \sum_{j=\tau_{i-1}+1}^{\tau_i} \lambda_j.$$

III. Maximum-Likelihood Estimator for Binned Data

We utilize a maximum-likelihood estimator (MLE) as our method to estimate $t = [t_1 \ t_2]^T$ directly from the raw data d. This allows us to avoid performing a log-normalization, which is not effective when any $d_i = 0$, whereas MLE is well-suited for such measurements. Since each $d_i$ is independent of any other and each is a Poisson distribution, the likelihood function is $$L_P(t) = f(d \mid t) = \prod_i \frac{\gamma_i^{d_i} e^{-\gamma_i}}{d_i!}. \quad (1)$$

Then the log-likelihood function is $$L_P^*(t) = \log f(d \mid t) = \sum_i (-\gamma_i + d_i \log \gamma_i - \log d_i!), \quad (2)$$

and we take our estimate of t to be $$\hat{t} = \operatorname*{argmax}_t L_P^*(t).$$

Estimator Performance

Because the measurements $\{d_i\}$ are noisy, the estimate $\hat{t}$ will be noisy. For a given t, we will show that the variance (a measure of imprecision, noise, or uncertainty) of $\hat{t}$ is a function of $\{\tau_i\}$, the energy bin cutoff thresholds, and that the variance can be minimized by selecting the appropriate $\{\tau_i\}$.

Error propagation allows us to approximate the variance in the estimate by using a first-order Taylor series expansion of $\hat{t}$ about t.

$$\operatorname{Cov}(\hat{t}_i, \hat{t}_j) \approx \sum_k \sum_l \left(\frac{\partial \hat{t}_i}{\partial d_k}\right)\left(\frac{\partial \hat{t}_j}{\partial d_l}\right) \operatorname{Cov}(d_k, d_l) \quad (3)$$

For binned data, the $\{d_i\}$ are independent of each other, so $$\operatorname{Cov}(\hat{t}_i, \hat{t}_j) \approx \sum_k \left(\frac{\partial \hat{t}_i}{\partial d_k}\right)\left(\frac{\partial \hat{t}_j}{\partial d_k}\right) \operatorname{Var}(d_k) \quad (4)$$

In Appendix A, the partial derivative terms in the above equation are shown so that the covariance can be explicitly computed. Note that if the photon counts were completely desegregated by energy, i.e., the number of counts at each energy can be measured independently, then we have the special case of N=M, and $\tau_0=0; \tau_1=1; \tau_2=2, \ldots, \tau_M=M$. We take this case of 1 keV bin sizes to be the ideal measurement, resulting in the least noisy estimate.

For a given $I_0, \mu_1, \mu_2$, and t, the precision of estimate t is a function of the bin energy cutoffs used. Given an objective, such as to minimize $\operatorname{Var}(t_1)$, which allows us to most precisely estimate $t_1$, we can search through the space of all bin cutoffs since our formulation only considers energies to the nearest keV. Hence, for a fixed N, we can find the $\{\tau_i\}$ that minimize the target objective function, where $0 < \tau_1 < \tau_2 < \ldots < \tau_{N-1} < M$ and $\tau_i \in \mathbb{N}, \forall Vi=1$. For N<5, searching through the space of possible $\{\tau_i\}$ is trivial, while it may take only a few minutes for N=7.

Numerical Example

Figure 2A:
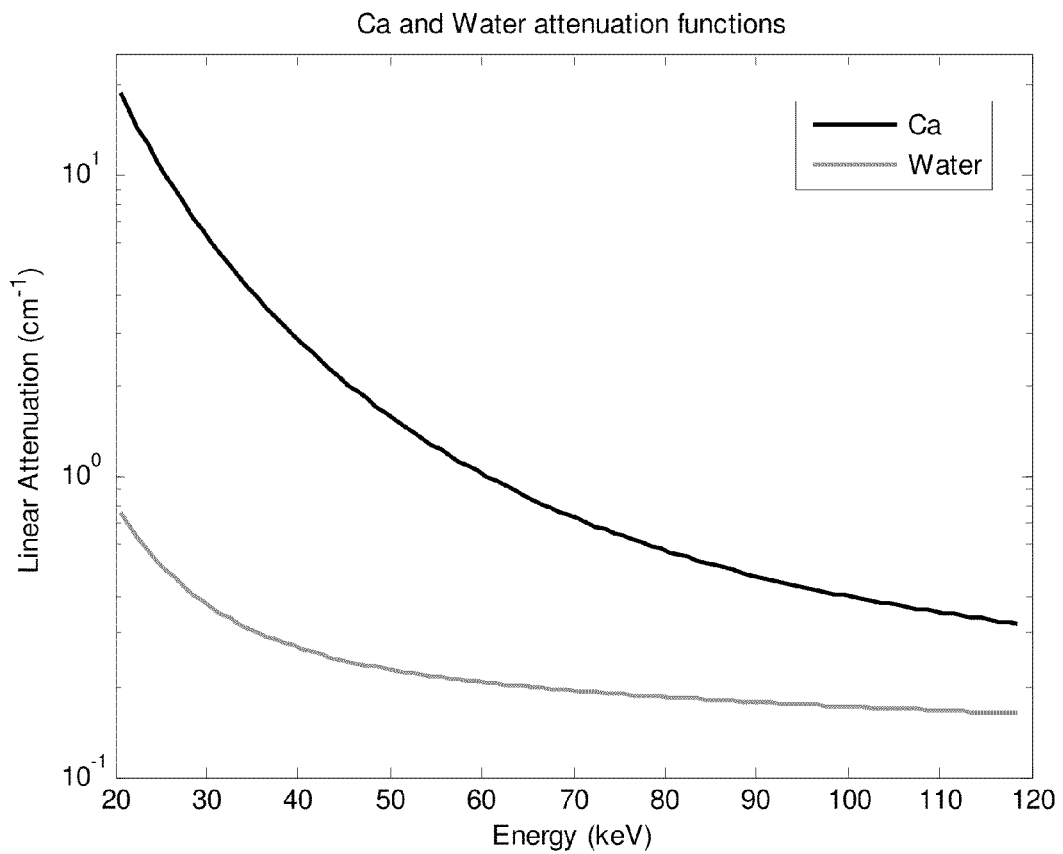
FIG. 2a shows the attenuation function of calcium and water.

To put this theoretical formulation to practice, we need to first select an $I_0$, $\mu_1$, $\mu_2$. Take $I_0$ to be a 120 kVp beam with an intensity equivalent to that of the photons that would fall on a single detector in a single view out of a CT scan with a 400 mAs exposure, as shown in FIG. 2a and FIG. 2b. FIG. 2a shows an attenuation function of calcium and water. FIG. 2b shows the incident spectrum. Calcium and water were chosen as two materials for these examples because decomposing attenuation into these two basis materials can have direct applications, such as bone densitometry or arterial plaque characterization. Furthermore, if indeed the underlying mechanisms for dual-energy material decomposition are the photoelectric and Compton attenuations functions, as is known in the art, we can easily convert our results from using calcium and water into any other two materials via a linear transformation.

Energies below 20 keV were ignored, since they are heavily filtered at the source and have very little penetrating ability for materials of non-trivial thickness. Furthermore, because the attenuation of photons below 20 keV rises rapidly, including this part of the curve in the analysis can result in poorly conditioned matrices that can introduce numerical errors. Finally, we take as our objective to predict as precisely as possible the amount of calcium, i.e. minimize $\text{Var}(\hat{t}_{Ca})$. Although more general objective functions could be selected, this objective is reasonable given that typically $t_{Ca} \ll t_{H_2O}$ and that often imaging tasks require precise estimation of calcium levels.

Figure 3:
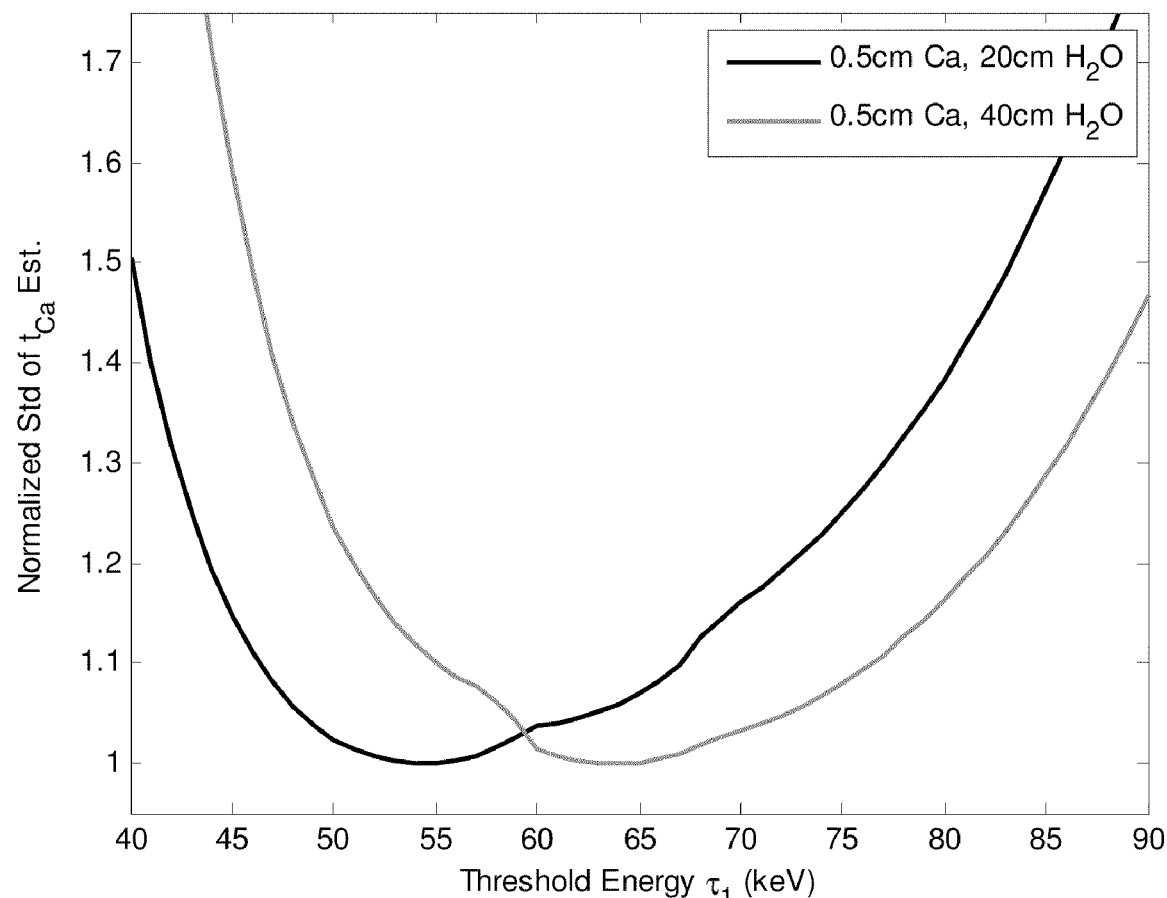
FIG. 3 shows the normalized standard deviation of $\hat{t}_{Ca}$ as a function of threshold energy $\tau_1$.

FIG. 3 shows the normalized standard deviation of $\hat{t}_{Ca}$ as a function of threshold energy $\tau_1$, for the case of two energy bins, 5 mm Ca, and water thicknesses of 20 cm and 40 cm. We can see that setting $t_1 = 54$ keV provides for the least noisy estimate of the amount of calcium for 5 mm Ca and 20 cm water, while at 5 mm Ca and 40 cm water, the optimal $t_1$ is 63 keV. Clearly, when we only have two energy bins, the selection of $t_1$ can significantly change the performance of our MLE, and the optimal threshold depends on the object being studied.

IV. Relaxation of Abutment Constraint

Above, we assumed that the N bins are separated by cutoff thresholds, suggesting that each bin i collects photons from the interval of energies $(\tau_{i-1}, \tau_i]$. Adjacent bins have adjacent, non-overlapping intervals that abut each other. However, we can relax this constraint by allowing bin i to collect photons from energies $(l_i, u_i]$, where $0 \leq l_1 \leq u_1 < l_2 \leq u_2 \leq \ldots \leq l_N \leq u_N \leq M$. Then, adjacent bins have non-overlapping intervals, but these intervals do not necessarily abut each other.

Figure 4:
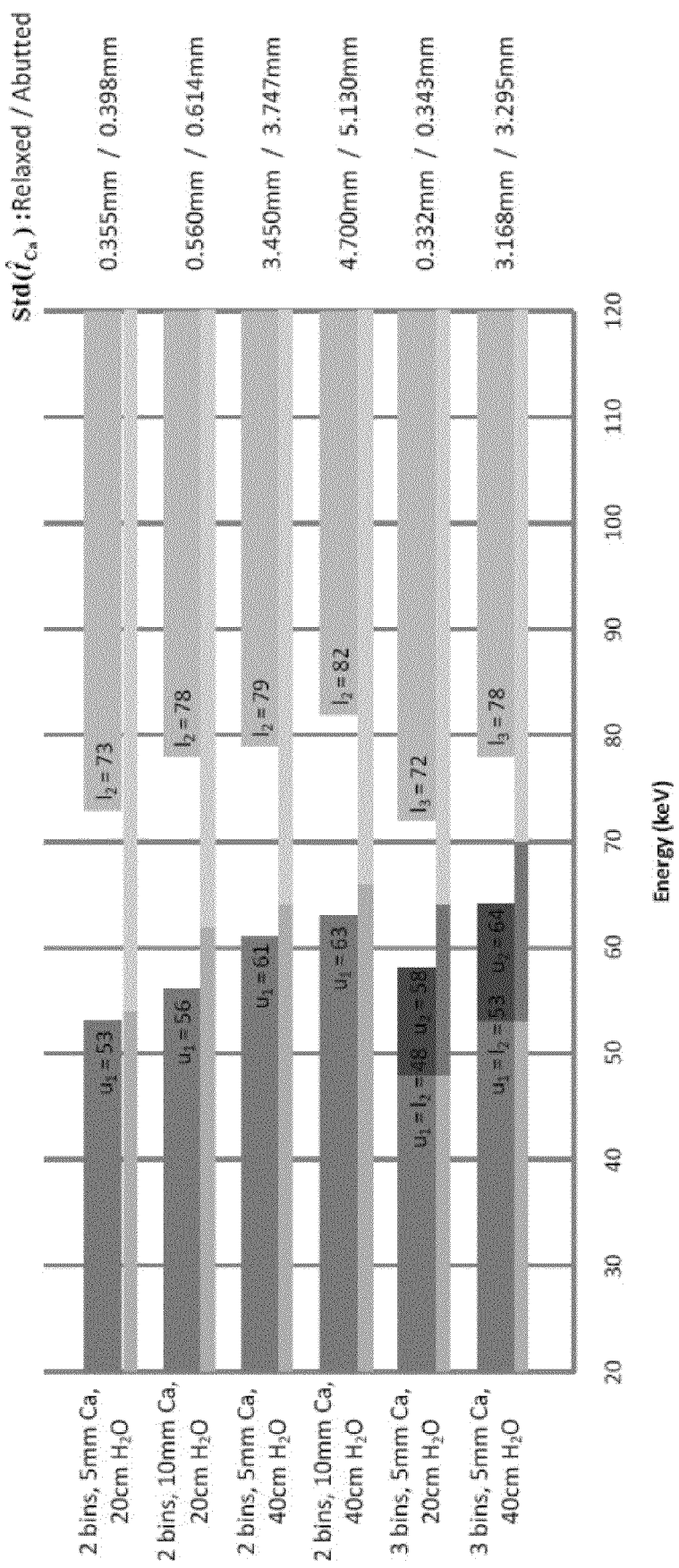
FIG. 4 shows a comparison for various cases of optimal thresholds when the abutment constraint is relaxed.

For our numerical example, we can again perform an exhaustive search through the space of $\{l_i, u_i\}$ to find the optimal thresholds. The resulting thresholds are shown in FIG. 4 for various thicknesses of calcium and water, as well as for two and three bins. FIG. 4 shows a comparison for various cases of optimal thresholds when the abutment constraint is relaxed, shown as thick bars, compared to when the abutment constraint is enforced, shown as thin bars. The standard deviation of $\hat{t}_{ca}$, $\text{Std}(\hat{t}_{ca})$, is listed for each case to the right of the chart. The most important result to note is that in the relaxed case, a significant portion of photons does not contribute to either binned measurement. When we consider two bins, the void between $u_1$ and $l_2$ represents energies where photons are ignored. Of course, adding a third bin can make use of some of the information contained here, but then there exists a void between $u_2$ and $l_3$. Without allowing such a void (by enforcing $u_1 = l_2$ and $u_2 = l_3$), the minimum $\text{Std}(\hat{t}_{ca})$ increases 10.8% from 0.355 mm to 0.398 mm in the first case. Adding a third bin brings $\text{Std}(\hat{t}_{Ca})$ closer to the ideal-case minimum of 0.308 mm. Lastly, we note that for thicker objects, the thresholds of the bins move to higher energies due to a beam hardening effect.

V. Weighted Measurements

We now generalize the concept of binning by allowing each detected photon to contribute a real-value amount to each "bin," depending on the photon's energy. Formally, for weights $w_{(i),j} \in \mathbb{R}$, the contribution of photons of energy j to bin i, the value of each bin measurement $d_i$ is given by $$d_i = \sum_j w_{(i),j} r_j = w_{(i)}^T r. \quad (5)$$

These weights can also be interpreted as the detector bins' response functions, as a function of energy. Binning counts as was done in the previous sections is a special case within the weighted measurements framework, with weights $w_{(i),j} = 1$ if $l_i < j \leq u_i$ and 0 elsewhere.

Because in general the measurements d are no longer Poisson distributed or uncorrelated, we model d with a multivariate Gaussian distribution: $d \sim N(e, \Sigma)$, where $e = E[d]$ and $\Sigma$ is the covariance matrix of d. This model is sound when the number of transmitted photons is not too low because each $d_i$ is the weighted sum of M independent Poisson random variables, where M is on the order of 100. Also, the first- and second-order moments of the model match those of d.

This leads us to a new likelihood function $$L_G(t) = f(d \mid t) = \frac{1}{(2\pi)^{(N/2)} |\Sigma|^{1/2}} \exp\left(-\frac{1}{2}(d-e)^T \Sigma^{-1}(d-e)\right) \quad (6)$$

The log-likelihood function is $$L_G^* = \log L_G(t) = -\frac{1}{2}(\log|\Sigma| + (d-e)^T \Sigma^{-1}(d-e)), \quad (7)$$

where the constant term is dropped.

Again, we can use error propagation to compute the variance of the estimate $\hat{t}$. The full expressions are shown in Appendix B.

Finding Optimal Weights

Finding the optimal weights for a given configuration $\{I_0, \mu_1, \mu_2, t\}$ requires a little more sophistication than before. We first note two aspects of the problem. First, we expect the optimal weights $w_{(1)}, \ldots w_{(N)}$ to be smooth over the energies since $\mu_1$ and $\mu_2$ are themselves smooth as a function of energy, barring a K-edge. When the attenuation curves are smooth, there is little difference in the ability of photons of nearby energies to discriminate the two materials. Therefore, we would not expect the weights of nearby energies to vary much.

Secondly, for weights $W = [w_{(1)}, \ldots w_{(N)}]$, our MLE performance is no different than if detector readings d' were acquired with weights $W' = WY^T$, where Y is a full-rank N×N matrix. This is because the readings that would have been acquired by using weights W can be recovered exactly through the relation $d = Y^{-1}d'$. Therefore, when searching for optimal weights, we must be careful to constrain them in such a way that we are searching for a unique solution.

Depending on the task or goal of the material decomposition, we can write a suitable objective function that we seek to minimize by varying the weights. We regularize the smoothness of the weights by adding a penalty proportional to the quadratic smoothness:

$$\phi(W) = \sum_{i=1}^{N} \sum_{j=1}^{M-1} (w_{(i),j+1} - w_{(i),j})^2. \quad (8)$$

For example, if our goal is to estimate $t_1$ as precisely as possible, then we would like to find weights W that minimize $\text{Var}(\hat{t}_1)+\eta\phi(W)$, where $\eta$ is the penalty proportionality constant. Furthermore, as mentioned before, we must constrain the weights to arrive at a unique solution. One simple approach is to arbitrarily fix N of the weights in $w_{(i)}$ for i=1, ..., N. After finding the solution with these constraints, we can of course form alternate weights W' through any full-rank matrix Y.

Although in general the objective function may not be convex, we use an approximation of Newton's method for optimization. While it is straightforward to evaluate the objective function for any set of weights, analytically finding expressions for its gradient vector and Hessian matrix can be tedious. Hence, we use numerical differentiation by evaluating the objective function at W and $W \pm \epsilon \delta_{ij}$ for all i, j, where $\epsilon$ is a small constant and $\delta_{ij}$ is a matrix whose element (i, j) is 1 and is zero elsewhere. Furthermore, to reduce computational time, the Hessian matrix is approximated by its diagonal. Finally, we relax the smoothness constraint after each iteration by reducing $\eta$ so that the smoothness constraint ultimately plays a small part compared to the intended objective.

Numerical Example

We consider two "bins" whose weights are initialized as two normalized ramp functions: $w_{(1)}$ goes linearly from 0 to 1, while $w_{(2)}$ goes linearly from 1 to 0. We fix the weights at energies 52 keV and 87 keV, approximately ⅓ of the total energy spread apart, so that the curves will be unique. The smoothness regularization parameter, $\eta$, is chosen so that $\eta\phi$ (W) is 10% of the initial objective function's value and is exponentially decreased with every iteration so that it halves with every 200 iterations. For comparison purposes, we are interested in finding optimal weights for an object equivalent to 5 mm Ca and 20 cm water. Since 20 cm of water significantly attenuates the lower energy photons, we add an additional term to the objective that prevents the contribution of the low energy weights from being dominated by the smoothness penalty. Our objective function is then:

$$\psi(W) = \text{Var}(\hat{t}_{Ca})\big|_{t=[.520]^T} + \text{Var}(\hat{t}_{Ca})\big|_{t=[00]^T} \frac{\text{Var}_{Ideal}(\hat{t}_{Ca})\big|_{t=[.520]^T}}{\text{Var}_{Ideal}(\hat{t}_{Ca})\big|_{t=[00]^T}}, \quad (9)$$

where $\text{Var}(\hat{t}_{Ca})$ is evaluated at the respective t with weights W, the fraction is a constant term that scales the second term to the same level as the first, and $\text{Var}_{Ideal}(\hat{t}_{Ca})$ is the variance of the ML estimate with ideal measurements.

Applying our approximate Newton's method to minimizing $\psi(W)+\eta\phi(W)$, we can quickly find smooth weights that begin minimizing the objective function. FIG. 5a-g are graphs of the weights as the search computation progresses: initial weights (FIG. 5a), the weights at iteration 100 (FIG. 5b), the weights at iteration 101 (FIG. 5c), the weights at iteration 626 (FIG. 5d), the weights at iteration 700 (FIG. 5e), and the optimal weights (FIG. 5f). FIG. 5g shows the value of the objective function versus iteration number. However, after 100 iterations, it is clear that the weight curves are deviating from the four fixed initial weights and now exhibit cusps. Since these cusps seem to be artificially induced, we "shave" them off to obtain smooth weights by estimating the weights in the cusp regions with a local polynomial fit. Doing this every 100 iterations appears to be an effective technique since there is a rapid drop in both the calcium estimate variance $\psi(W)$ and the smoothness penalty $\phi(W)$ after each "shave" (FIG. 5g).

If we continue to run Newton's method for many iterations, high frequency oscillations in the weights eventually begin to appear, possibly due to numerical or round-off errors. These errors make the smoothness penalty and objective function rise rapidly, at which point our method is no longer updating the weights in a useful direction. Fortunately, before this occurs, the minimum $\psi(W)$ at iteration 626 is a sufficiently close solution to the ideal minimum. After smoothing out the cusps at the fixed points, we arrive at an optimal set of weights $\hat{W}=[\hat{w}_{(1)} \hat{w}_{(2)}]$ (FIG. 5f).

Optimal Weights Performance

We tested this method of weighted binning of PCXD data by simulating noisy data and examining the performance of our MLE in estimating t. The system of equations in (12) in Appendix B describes the MLE solution for estimating t from the weighted binning data. Solving this non-linear system of equations analytically is not straightforward. Instead, we again use Newton's method to find the maximum of $L^*_G$. The expression for the gradient of the MLE was already found for (12), and the Hessian matrix can be similarly found. Although the MLE function is not convex in t, we found that it is well-behaved, and the Newton method works well in finding the maximum.

For $t=[0.5\ 20]^T$, we generated 10,000 realizations of ideally measured noisy data $\{r_1, r_2, \ldots, r_M\}$ and the corresponding weighted measurements $\{\hat{d}_1, \hat{d}_2\}$ using optimal weights $\hat{W}$. The resulting MLE estimates of t for each sample are displayed in FIG. 6a-b, which show plots of MLE estimates of t using the optimal weights (FIG. 6a) or using ideal 1 keV bins (FIG. 6b). The sample variances and covariance of the estimates, which are shown in Table I, show that the empirical performance of the optimal weights match that of the ideal 1 keV bins, all well within 1% of each other.

TABLE 1

Comparison of Empirical Performance to Predicted Theory for $t_{Ca} = 0.5$ cm, $t_{H2O} = 20$ cm.

| | Var ($\hat{t}_{Ca}$) | Var ($\hat{t}_{H2O}$) | Cov ($\hat{t}_{Ca}, \hat{t}_{H2O}$) |
|---|---|---|---|
| Empirical, Ideal | $9.511 \times 10^{-4}$ | $2.241 \times 10^{-2}$ | $-4.196 \times 10^{-3}$ |
| Empirical, Weights | $9.519 \times 10^{-4}$ | $2.241 \times 10^{-2}$ | $-4.198 \times 10^{-3}$ |
| Predicted, Ideal | $9.464 \times 10^{-4}$ | $2.256 \times 10^{-2}$ | $-4.200 \times 10^{-3}$ |
| Predicted, Weights | $9.457 \times 10^{-4}$ | $2.255 \times 10^{-2}$ | $-4.197 \times 10^{-3}$ |

While these weights have near-optimal performance for estimating calcium thickness at 5 mm Ca, 20 cm water, it is not clear how they will perform at estimating water or for other thicknesses. We can examine this by finding the theoretical variance of the estimates at various thicknesses using W and comparing it to the theoretically predicted variance of the estimates resulting from our ideal 1 keV binning that completely desegregates the photon counts of different energies, as shown in Table I. Furthermore, for the variances and the covariance of the estimates $\hat{t}_{Ca}$ and $\hat{t}_{H_2O}$, we normalize the performance of optimal weights $\tilde{W}$ by dividing the equivalent figure of merit for the ideal measurements and plot these over a wide range of diagnostically relevant t. FIG. 7 a-d are graphs of the performance of optimal weights as a function of t, normalized to ideal performance versus normalized Var($\hat{t}_{Ca}$), FIG. 7a, normalized Var ($\hat{t}_{H_2O}$), FIG. 7b, normalized Cov($\hat{t}_{Ca}$, $\hat{t}_{H_2O}$), FIG. 7c, and normalized Var($\hat{t}_{ca}$),$I_0$=20$I_0$. As can be seen, the values for weighted binning are essentially equal to unity over most of the range of thicknesses. Thus, even though the weights were computed for one object (5 mm Ca, 20 cm water), theory predicts that weighted binning with these weights performs as well as the original data over a wide range of objects. Note that for thick objects the analytical prediction of performance predicts variances lower than those of the ideal case, which cannot be correct. We believe that the Gaussian model used in (6) may be violated when very few photons penetrate the object, causing the predicted variance from the optimally weighted measurements to be less than that of the ideal case. In support of this hypothesis, we found that if we scale the incident intensity $I_0$ by a factor of 20, this problem largely disappears (FIG. 7d).

Nonetheless, our results suggest that using weights W to measure only two parameters, $\{\tilde{d}_1, \tilde{d}_2\}$, for any thicknesses of calcium and water, we can estimate $\{t_{ca}, t_{H_2O}\}$ as well as if we knew the detected photon counts at every energy. This allows us to "compress" a tremendous amount of data (the counts at each energy) into a much smaller number of values ($d_1$, $d_2$). Even though weights $\tilde{W}$ are optimized for 5 mm Ca, 20 cm water and to minimize Var($\hat{t}_{Ca}$), they are in fact optimal for any amount of any two materials, simply as long as the attenuation of these materials can be expressed as a linear combination of the attenuation of calcium and water because estimates from data measured with weights $\tilde{W}$ have the same variances and covariance as the ideal measurements. However, note that finding optimal weights $\tilde{W}$ may depend on the shape of the incident spectrum. If $I_0$ is changed, then the weights we computed may no longer be optimal.

VI. Discussion

Figure 8:
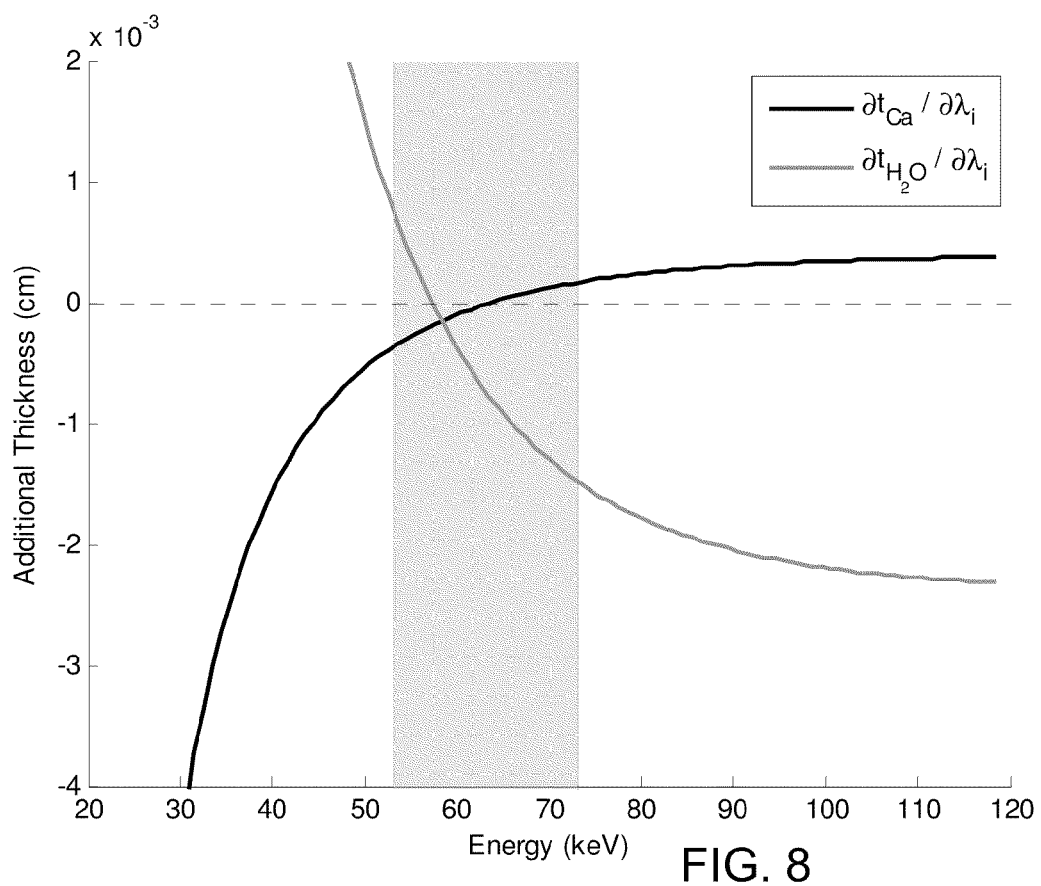
FIG. 8 is a graph of the change in estimated thickness using ideal measurements for an additional photon detected at 5 mm Ca and 20 cm water versus energy.

Our first main result is that relaxing the abutment constraint for binning thresholds can improve material decomposition performance of binned data by allowing some photons to be discarded. The benefit of this void region can be understood by examining the sensitivity of each material thickness estimate to an additional photon at various energies with ideal measurements. FIG. 8 illustrates this by showing a graph of the change in estimated thickness using ideal measurements for an additional photon detected at 5 mm Ca and 20 cm water versus energy. When we only have two energy bins, additional photons in $d_2$ decrease the water estimate and increase the calcium estimate while doing the opposite for additional photons in $d_1$ because calcium has a relatively higher attenuation than water at lower energies than at higher energies. Our MLE for ideal measurements has very little sensitivity to photons in the void region (shaded region in the figure). Including photons in the shaded region into either of two bins adds noise while providing little sensitivity to material separation. Hence, the precision of the estimator using $\{d_1, d_2\}$ is improved if we do not count certain photons into either bin.

Figure 9:
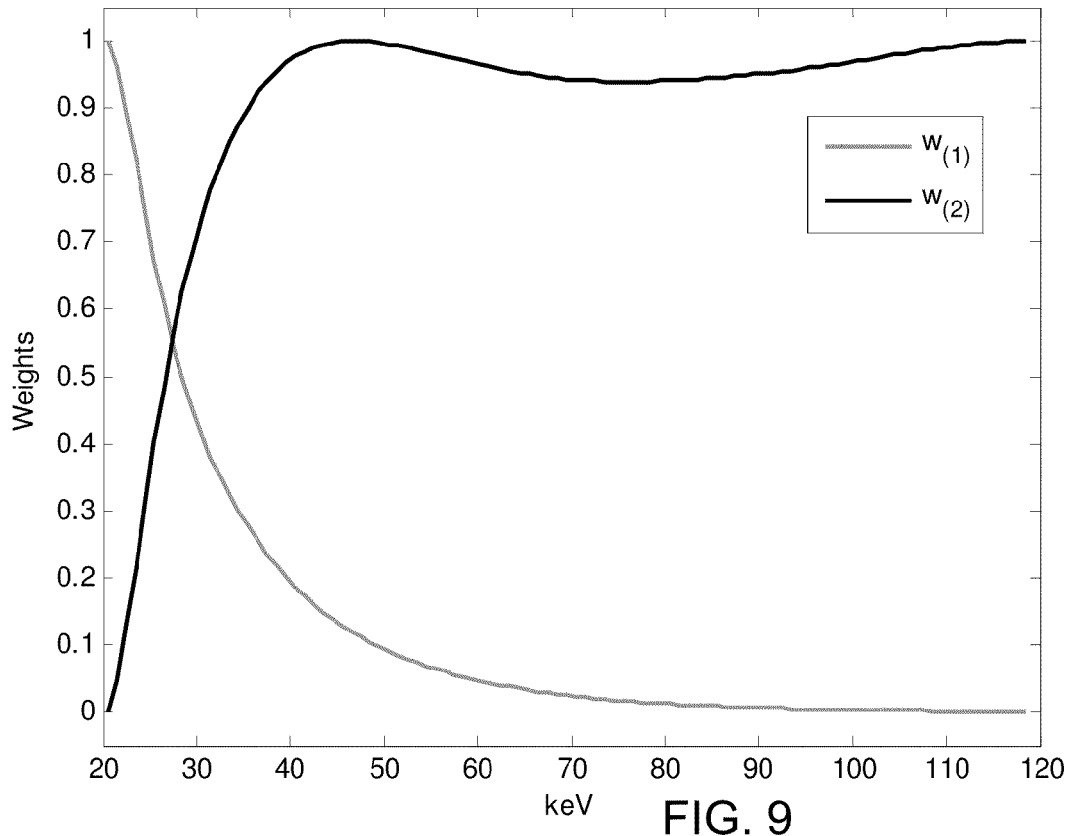
FIG. 9 is a graph of equivalent optimal weights $\tilde{W}'$, where $\tilde{w}'_{(1)}$ goes from 1 to a minimum of 0, and $\tilde{w}'_{(2)}$ goes from 0 to a maximum of 1.

Our second main result is the experimental observation that optimal weights $\tilde{W}$ can be found that condense all of the photon counts and energy information into two measurements $\{\tilde{d}_1, \tilde{d}_2\}$ and still allow for t to be estimated as well as if we had ideal measurements of all photons. As mentioned before, since any full-rank matrix Y can transform weights $\tilde{W}$ into another set of optimal weights, it is not immediately clear what these weights represent. However, we can present them in a more standard way, by finding equivalent optimal weights $\tilde{W}'$, where $\tilde{w}_{(1)}$ goes from 1 to a minimum of 0, and $w_{(2)}$ goes from 0 to a maximum of 1 (FIG. 9). These then represent a "low" and "high" energy measurement, although photons from all energies contribute to both measurements.

VII. Analytical Form and Theoretical Basis

The method described above finds the optimal weights using a computational approach. An analytical formalism is also possible. To show that the invention provides the exact analytical form and theoretical basis of the numerically derived weights, we will show that the optimal weights are in fact the same as the attenuation basis functions.

For objects that can be decomposed into two materials of thicknesses $t_1$ and $t_2$ with attenuation $\mu_1(E)$ and $\mu_2(E)$, respectively, the expected number of transmitted photons for a known incident spectrum $I_0(E)$ is:

$$\lambda(E) = I_0(E)\exp(-t_1\mu_1(E) - t_2\mu_2(E)),$$

while the number of photons actually detected is a Poisson random variable $r(E) \sim \text{Poisson}(\lambda(E))$.

To say that, for optimal weights $w_1$ and $w_2$, the two measurements $d_1 = w_1^T r$ and $d_2 = w_2^T r$ allow us to estimate t as well as r can, is equivalent to the notion that $\{d_1, d_2\}$ is a sufficient statistic for t. Thus, a sufficient statistic captures all the information about t that r would contain. The concept of sufficient statistics is described, among others, in the book *Statistical Inference* by G. Casella and R. L. Berger, published by Duxbury Press, 1990. A statistic D(r) is a sufficient statistic for t if and only if there exist functions g(d|t) and h(r) such that, for all r and t, $$f(r|t) = h(r)g(D(r)|t),$$

where f(r|t) is the joint pdf of r.

Let us consider energies to the nearest keV and denote energy with a subscript. Because each $r_E = r(E)$ is independent from those of different energies, the joint pdf is the product of Poisson distributions:

$$f(r|t) = \prod_{i=1}^{M} f(r_i|t)$$

$$= \prod_{i=1}^{M} \frac{e^{-\lambda_i}\lambda_i^{r_i}}{r_i!}$$

$$= \prod_{i=1}^{M} \frac{e^{-\lambda_i}(I_{0,i}\exp(-t_1\mu_{1,i} - t_2\mu_{2,i}))^{r_i}}{r_i!}$$

$$= \left(\prod_{i=1}^{M} \frac{I_{0,i}^{r_i}}{r_i!}\right)\exp\left(-\sum_{i=1}^{M}\lambda_i - t_1\sum_{i=1}^{M}\mu_{1,i}r_i - t_2\sum_{i=1}^{M}\mu_{2,i}r_i\right)$$

$$= h(r)g(D(r)|t)$$

where $h(r) = \left(\prod_{i=1}^{M} \frac{I_{0,i}^{r_i}}{r_i!}\right)$, $$g(D(r)|t) = \exp\left(-\sum_{i=1}^{M}\lambda_i - t_1\sum_{i=1}^{M}\mu_{1,i}r_i - t_2\sum_{i=1}^{M}\mu_{2,i}r_i\right), \text{ and}$$

$$D(r) = [d_1 \ d_2]^T = \left[\sum_{i=1}^{M}\mu_{1,i}r_i \ \sum_{i=1}^{M}\mu_{2,i}r_i\right]^T = [\mu_1 \ \mu_2]^T r.$$

Therefore, we have proven that using the attenuation basis functions $\mu_1$ and $\mu_2$ (or any linear combination of the two) as the weights provides a sufficient statistic for estimating t. If there are more than two attenuation basis functions, then it is easy to see that using each as a weighting function will result in measurements that are a sufficient statistic. We call these weights μ-weights.

VIII. Comparison

Performance Curves

Performance bounds on basis material decomposition for any given system and detector configuration can be derived from the Cramer-Rao lower bound (CRLB). For any unbiased estimate $\hat{t}$ with corresponding covariance matrix $C_{\hat{t}}$, the CRLB C provides a lower bound so that $C_{\hat{t}} \geq C$ in the matrix inequality sense. The CRLB can be computed by taking the inverse of the Fisher information matrix, which can be computed analytically from the maximum-likelihood functions.

The CRLB for the full spectrum $C_F(t)$ represents the absolute minimum covariance performance of any unbiased estimate of the material decomposition for any information collection scheme, including binning and weighted measurements. We can compare the CRLB $C_B(t)$ of any binning scheme to that of $C_F(t)$, the CRLB for the full detected spectrum, to illustrate the suboptimality in estimating t when binning the detected spectrum. If we normalize $C_B$ by $C_F$, we get a penalty factor $Q_B$ for binning. Then, for instance, $Q_{B,11}(t) = C_{B,11}(t)/C_{F,11}(t)$ represents how much higher the best case variance of the estimated amount of calcium, $\hat{t}_{Ca}$, will be as a result of binning the full detected spectrum since $C_{B,11}$ corresponds to the minimum variance of estimate $\hat{t}_1$ when binning and we take calcium as material 1. Similarly, we can compare the CRLB $C_W(t)$ of any weighted measurements to that of $C_F(t)$ to illustrate the suboptimality in estimating t when forming weighted measurements of the detected spectrum.

Under the two basis material assumption, using μ-weighted measurements requires two measurements from the detector. Therefore, for comparison, we assess the performance from using two binned measurements. We also include in the comparison the performance of a photon counting and energy integrating x-ray (CIX) detector, which measures the total number of incident photons (photon counting) and also the total energy of the incident photons (energy integrating). Therefore, it effectively makes two measurements with weighting functions of $w_{(1)}(E)=1$ and $w_{(2)}(E) \propto E$—that is, the first weighting function is 1 for all energies, and the second weighting function is proportional to the energy of the photons.

FIG. 10a-e are graphs of the CRLB performance for different weighing schemes, with different contour levels in the subfigures. Consider a range of medically relevant t ($0 \leq t_{Ca} \leq 2$ cm, and $0 \leq t_{H2O} \leq 40$ cm). For the 120 kVp spectrum, as shown in FIG. 2a, the minimum achievable $\hat{t}_{Ca}$ variance (in units of cm$^{-2}$) as given by $C_{F,11}$ as a function of the amount of water and calcium is shown in FIG. 10a as log contour lines. The calcium estimate uncertainty increases with increasing object attenuation. FIG. 10b shows the penalty function $Q_{B,11}$ (the increase in the variance of $\hat{t}_{Ca}$) when two bins are used with a fixed threshold of 57 keV, the threshold that minimizes the maximum (over t) penalty factor, and FIG. 10c shows similar data for the CIX detector. Binning with a threshold of 57 keV incurs a penalty of a factor of 3.4 at the lower left corner t=(0, 0) and of at least a factor of 1.7 throughout. A CIX detector incurs lower penalties, especially at larger t but still incurs a penalty of at least 22% and up to a factor of two in Var($\hat{t}_{Ca}$).

The ratio of $C_W$ to $C_F$ for μ-weights when using the Gaussian model is shown in FIG. 10d for Var($\hat{t}_{Ca}$). This ratio is near 1 at low object thickness, as expected, but drops below 1 for thicker objects. However, we know that any unbiased estimator using the μ-weighted measurements cannot truly have better performance than an estimator having knowledge of the full detected spectrum. Therefore, we conclude that the commonly used multivariate Gaussian model may not be fully accurate for weighted measurements when the number of photons detected is low. For example, the expected number of photons detected for the thickest object t=(2, 40) is only 39 photons. Poisson distributions with low mean counts can only take on a set of discrete values and are positively skewed, unlike Gaussian distributions. This conclusion is supported by the fact that the exact CRLB of the μ-weighted measurements as provided by the empirical characteristic function method described in Appendix C is well within 0.1% of the CRLB of the full detected spectrum (FIG. 10e). The accuracy of this method simply depends on the discretization of the Fourier space variable s and becomes a numerical issue.

These results show that μ-weighted measurements achieve the same performance in estimating $\hat{t}_{Ca}$ as knowledge of the full spectrum. We have also found that, the Cov($\hat{t}_{Ca}, \hat{t}_{H2O}$) and Var($\hat{t}_{H2O}$) for μ-weighted measurements also match those of the full spectrum, while those of binning and the CIX exhibit similar penalty ratios to their Var($\hat{t}_{Ca}$) counterparts under the different measurement schemes.

We note that it is possible to have objects that decompose into a negative amount of calcium or water. While only quadrant I ($t_{ca}, t_{H2O} \geq 0$) of the calcium/water decomposition space is shown in FIG. 10a-e, our results extend smoothly into the valid regions of quadrants II and IV, and none of our methods preclude negative amounts of either basis material.

B. Wedge Phantom

We also simulated the dual-energy performance of the three different binning or weighting schemes on a phantom designed to compare the calcium detectability of the methods. Consider a projection image with 0.2 mAs exposure of a water wedge phantom varying from 0 to 40 cm thickness in the horizontal (x) direction with square calcium contrast elements ranging in area from 1 mm$^2$ to 1 cm$^2$ overlaid on top. FIG. 11 a-f show this wedge phantom, FIG. 11a, a true $t_{Ca}$ graph, a window Ω versus horizontal location graph and common thickness estimations with different weighing schemes, displayed on varying grayscale range [−Ω(x)+Ω(x)], FIG. 11d-f. These elements have a thickness such that the predicted (full area) SNR of each calcium element from the full detected spectrum is 4 (at the threshold of detectability). Because the necessary amount of calcium to maintain a constant SNR increases as the water gets thicker and as the elements becomes smaller, the calcium images are displayed on a spatially varying grayscale window [−Ω(x)+Ω(x)] in the horizontal (x) direction, where Ω is specified as a function of horizontal position x (FIG. 11b,c). Transmission of the x-ray spectrum and detection with energy resolution of 1 keV and perfect detection efficiency was simulated. Noise was injected based on Poisson distributed measurements in each energy interval. The simulated detected spectra were then subjected to each of the measurement schemes.

Maximum-likelihood estimation (MLE) is a commonly used method for estimating t given noisy measurements d and was a convenient choice given the extensive use of the log-likelihood functions in deriving the CRLB. We used Matlab's Optimization Toolbox (v3.1.1) to find the maximum-likelihood solution $$\hat{t}(d) = \underset{t}{\mathrm{argmax}}\, L^*(t\,|\,d). \quad (9)$$

Although more sophisticated methods may exist for estimating t, these are beyond the focus of this application. For the CIX and weighted measurements, we used the Gaussian model because the gradient and Hessian of the log-likelihood function are readily available in analytical form. We compare the ML decomposition of measurements taken with: (1) two abutted bins with a 57 keV threshold; (2) a CIX detector (i.e., $w_1=1$, $w_2\,\alpha E$); (3) µ-weights.

The resulting ML decompositions for the calcium component are shown in FIG. 11$d$-$f$. Detection of the targets is challenging in all the images since the phantom was designed to make this so, but the µ-weighted image is noticeably superior. The images illustrate that using µ-weights to form two measurements allows for increased conspicuity of all contrast elements as compared with a two bin or CIX approach. Because the calcium thicknesses of the elements span a large range, the estimates are also shown with the spatially varying grayscale window $[-\Omega(x)+\Omega(x)]$. As expected from the CRLB comparisons, FIG. 10$a$-$e$, the noise in the calcium image is highest when using two bins and lowest when using µ-weights. Thus, the SNR is highest when we use µ-weights to take weighted measurements.

IX. Conclusion

PCXDs offer a wealth of information about the object being measured that traditional energy integrating detectors cannot assess. The invention offers new insight into increasing the precision of material or basis function decomposition from binned or weighted measurements by providing the theoretical groundwork to predict estimator performance and then the methods to optimize the performance. Interestingly, we found that having a gap between energy thresholds can improve the precision of the system. Photons with energies that fall into this gap should either be discarded or counted separately to improve material separability.

Moreover, when estimating the amount of each of two material basis functions, two appropriately weighted sums of the photon counts provide as much information as knowing the number of counts at each energy. Through theoretical predictions and empirical measurements, we showed that for a given x-ray spectrum, these weights are optimal for any amount of any two materials, as long as these materials can be expressed as a linear combination of photoelectric and Compton attenuation.

X Generalized Flow Chart

Figure 12:
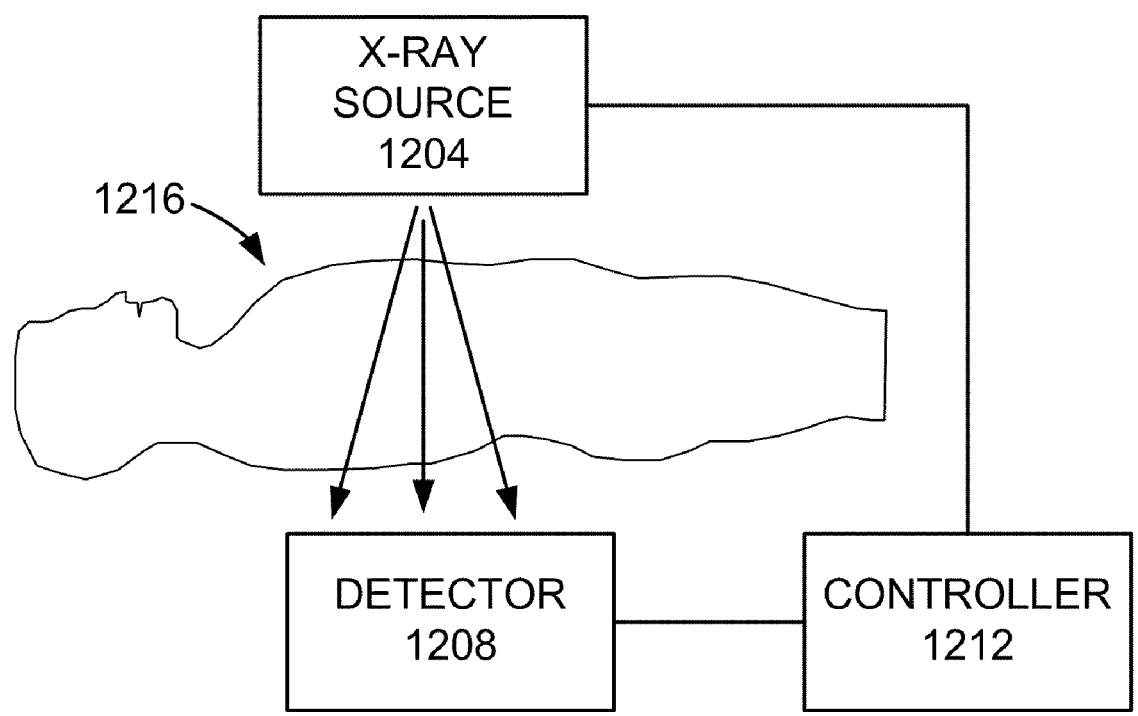
FIG. 12 is a schematic illustration of a CT system that may be used in an embodiment of the invention.

The invention may have various embodiments. One use of the invention may be for computed tomography (CT) or other x-ray systems such as a baggage scanner. FIG. 12 is a schematic illustration of a CT system or x-ray system that may be used in an embodiment of the invention. The system has a x-ray source 1204 that provides x-ray photons of at least two different energies, a detector which is able to detect x-ray photons and estimate the energy of the photons, such as a PCXD. The x-ray source 1204 and/or the detector 1208 may be a single x-ray source and/or detector or an array of sources and/or detectors. A controller 1212 is controllably connected to the x-ray source 1204 and detector 1208, so that the controller 1212 can control the x-ray source 1204 and the detector 1208 and receive data from the detector 1208. An object 1216, such as a human body may be disposed between the x-ray source 1204 and detector 1208.

Figure 13A:
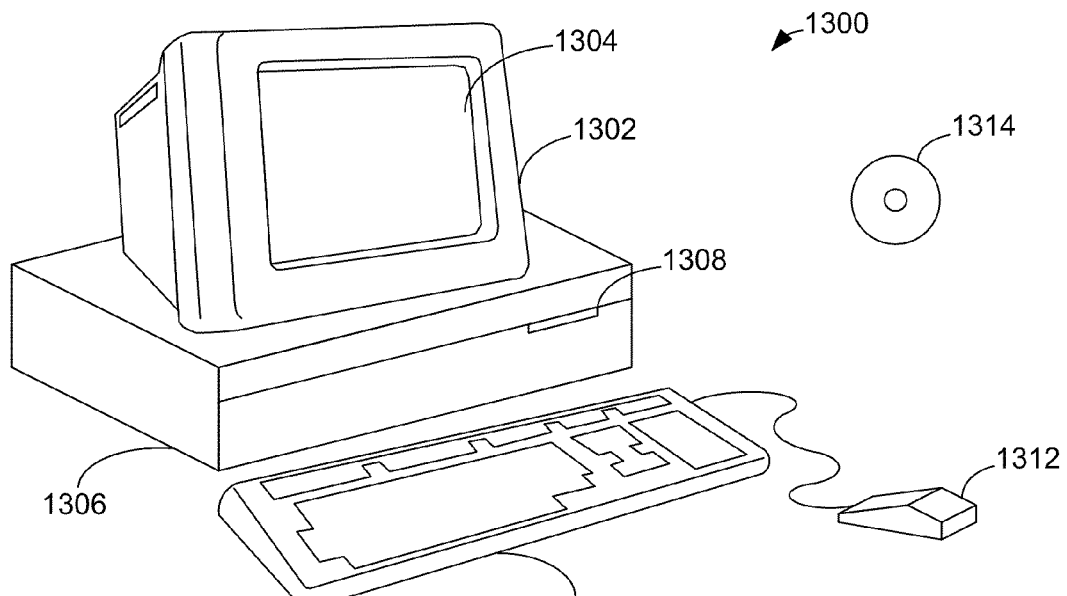
FIG. 13a-b illustrate a computer system, which is suitable for controlling a CT system.
Figure 13B:
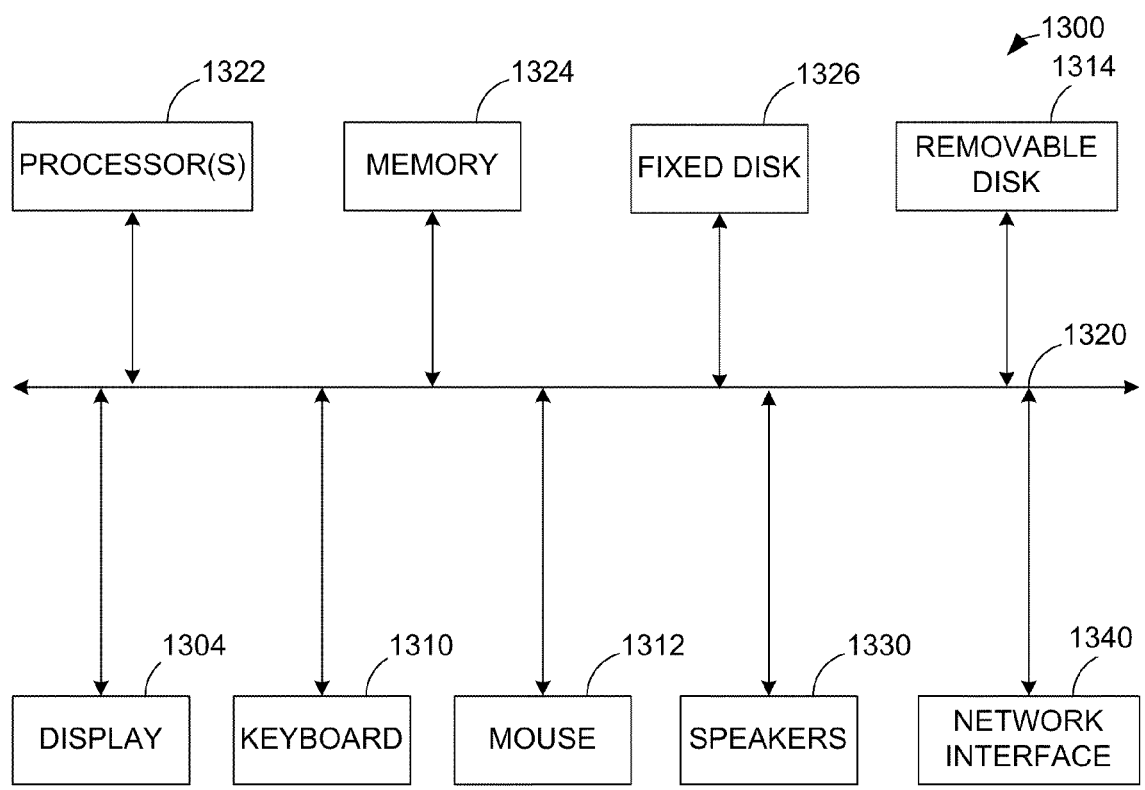

FIGS. 13$a$ and 13$b$ illustrate a computer system 1300, which is suitable for controller 1212 in embodiments of the present invention. FIG. 13$a$ shows one possible physical form of the computer system. Of course, the computer system may have many physical forms ranging from an integrated circuit, a printed circuit board, and a small handheld device up to a huge super computer. Computer system 1300 includes a monitor 1302, a display 1304, a housing 1306, a disk drive 1308, a keyboard 1310, and a mouse 1312. Disk 1314 is a computer-readable medium used to transfer data to and from computer system 1300.

FIG. 13$b$ is an example of a block diagram for computer system 1300. Attached to system bus 1320 are a wide variety of subsystems. Processor(s) 1322 (also referred to as central processing units, or CPUs) are coupled to storage devices, including memory 1324. Memory 1324 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any of the computer-readable media described below. A fixed disk 1326 is also coupled bi-directionally to CPU 1322; it provides additional data storage capacity and may also include any of the computer-readable media described below. Fixed disk 1326 may be used to store programs, data, and the like and is typically a secondary storage medium (such as a hard disk) that is slower than primary storage. It will be appreciated that the information retained within fixed disk 1326 may, in appropriate cases, be incorporated in standard fashion as virtual memory in memory 1324. Removable disk 1314 may take the form of the computer-readable media described below.

CPU 1322 is also coupled to a variety of input/output devices, such as display 1304, keyboard 1310, mouse 1312, and speakers 1330. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 1322 optionally may be coupled to another computer or telecommunications network using network interface 1340. With such a network interface, it is contemplated that the CPU might receive information from the network, such as CT raw data, or might output information to the network, such as reconstructed images, in the course of performing the above-described method steps. Furthermore, method embodiments of the present invention may execute solely upon CPU 1322 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of tangible computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 14:
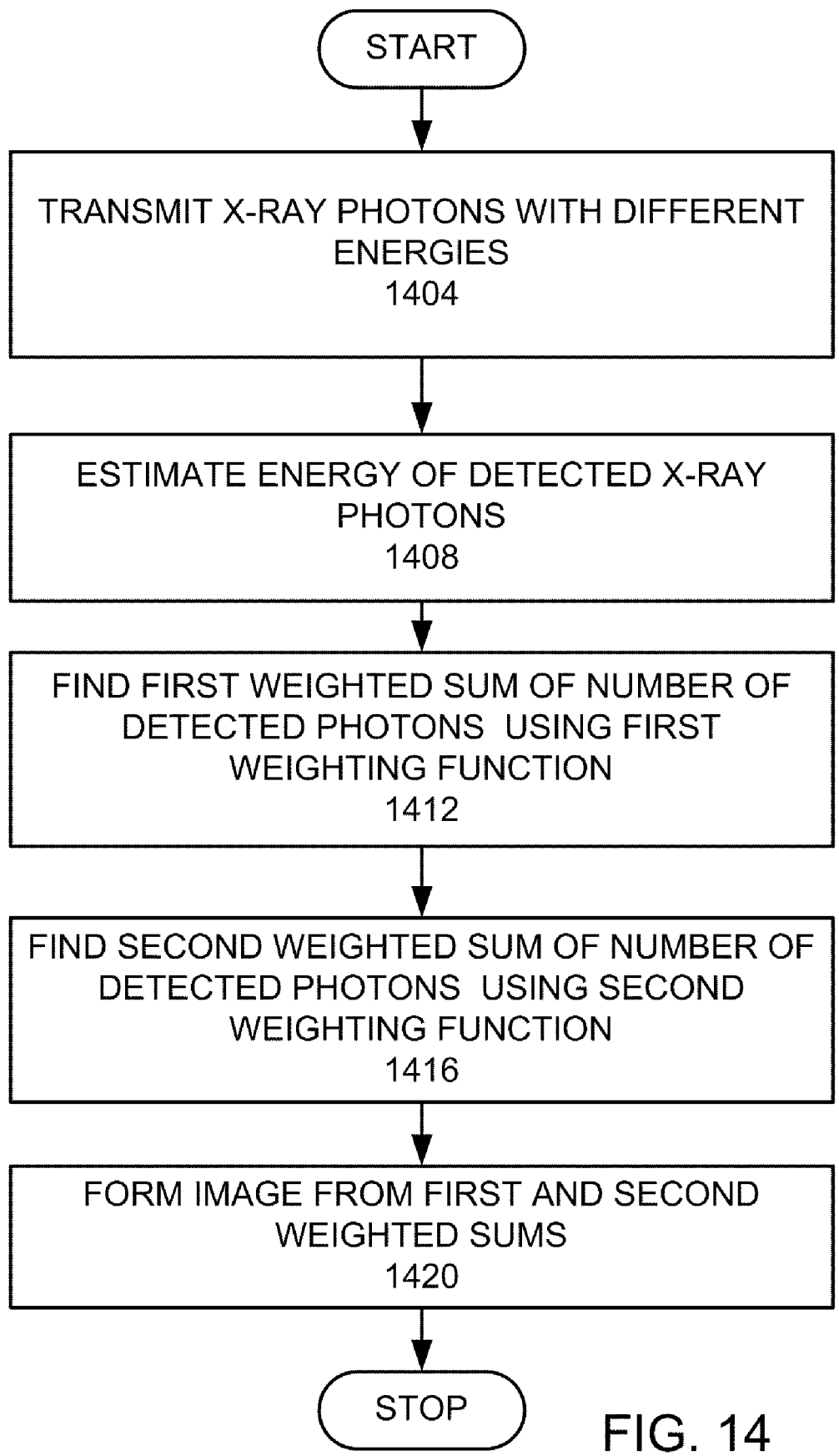
FIG. 14 generalized flow chart for an embodiment of the invention.

A generalized flow chart for an embodiment of the invention is illustrated in FIG. 14. X-rays photons with at least two different energies are transmitted (step 1404). The x-rays are provided by the x-ray source 1204. The x-ray photons are detected and the energies of the detected x-ray photons are estimated (step 1408). The x-ray photons are detected by the detector 1208. Preferably, the x-rays pass through an object 1216, before they are detected by the detector 1208. A first weighted sum of the number of detected photons is found using a first weighting function (step 1412). The first weighting function is dependent on an attenuation coefficient of a first material. One example of such a sum is $$\int_0^\infty S(E)w_1(E)dE,$$

where S(E) is the number of detected photons of energy E, $w_1(E)$ is the first weighting function. A second weighted sum of the number of detected photons is found using a second weighting function (step 1416). The second weighting function is dependent on an attenuation coefficient of a second material different from the first material. One example of such a sum is $$\int_0^\infty S(E)w_2(E)dE,$$

where $w_2(E)$ is the second weighting function. Preferably, the first weighting function is proportional to the attenuation coefficient function of the first material. It could also be a linear combination of the attenuation coefficient function of the first material and the attenuation coefficient function of the second material. Preferably, the second weighting function is proportional to the attenuation coefficient function of the second material. It could also be a linear combination of the attenuation coefficient function of the first material and the attenuation coefficient function of the second material that is linearly independent from the first weighting function. An image or images are formed from the first and second weighed sums (step 1420). Preferably, the image(s) result from a dual energy decomposition of the first and second weighted sums. The formed image(s) may be an image on a display 1304 or a printed on a print or may be formed some other way. The image(s) would be of the object 1216 through which the x-ray photons passed.

Figure 15:
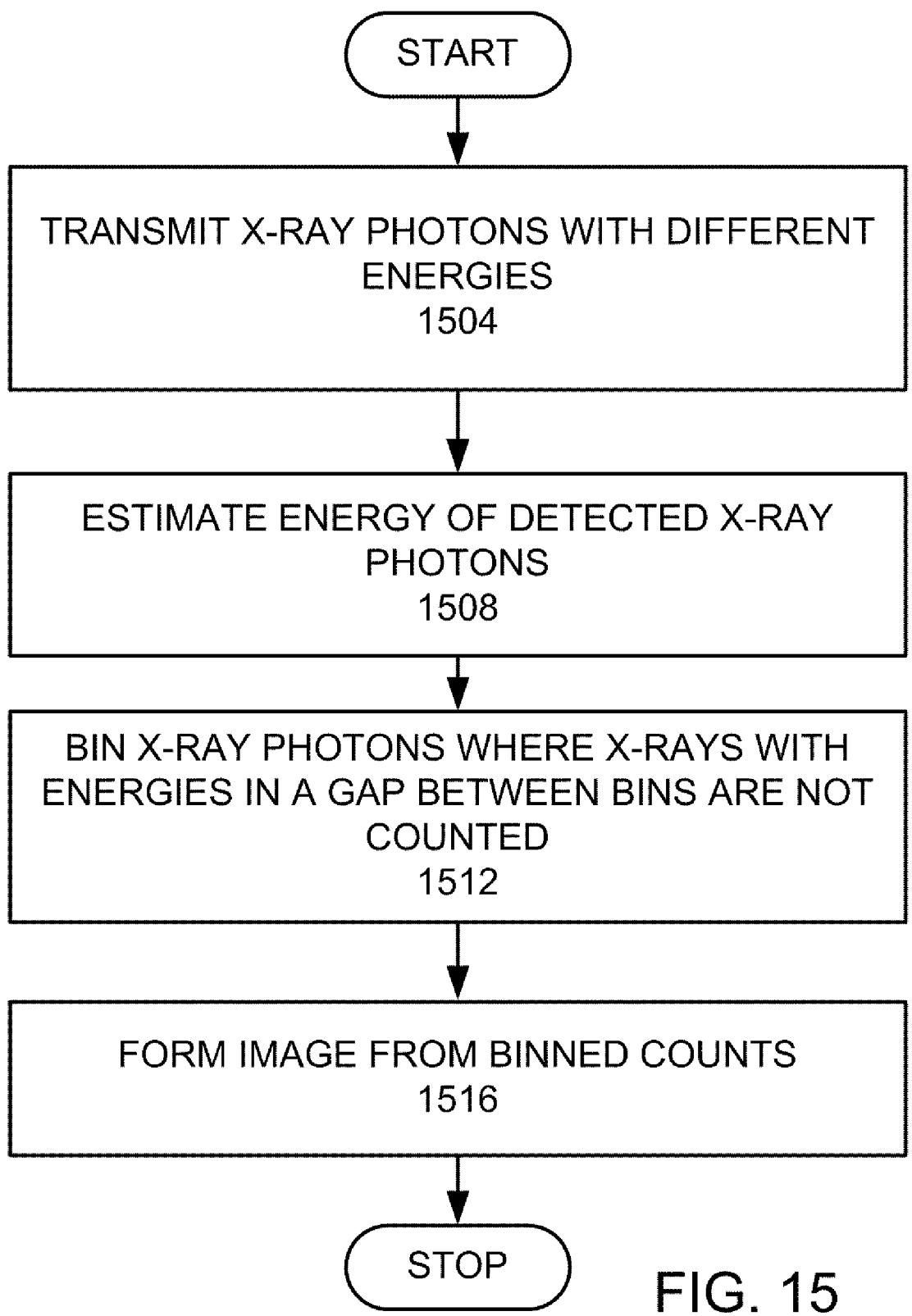
FIG. 15 generalized flow chart for another embodiment of the invention.

A generalized flow chart for another embodiment of the invention is illustrated in FIG. 15. X-rays photons with at least two different energies are transmitted (step 1504). The x-rays are provided by the x-ray source 1204. The x-ray photons are detected and the energies of the detected x-ray photons are estimated (step 1508). The x-ray photons are detected by the detector 1208. Preferably, the x-rays pass through an object 1216, before they are detected by the detector 1208. The x-ray photons are binned according to energy in at least two bins, where a gap is between energy thresholds between two bins, where photons with energies corresponding to the gap are not counted in any bin (step 1512). The binned data may be used to form an image (step 1516).

Should an additional material with attenuation $\mu_3$ deviate from the two basis material assumption, such as a material with a K-edge, be used as a basis function, the sufficient statistic proof, as described in Section VII Analytical Form and Theoretical Basis, can easily be extended to show that only three weighted measurements are needed. The first two weighting functions can be the same as before, but the third weighting function must depend on the third attenuation function $\mu_3$. In general, the three weighting functions can be linearly independent combinations of the three attenuation functions $\mu_1$, $\mu_2$, and $\mu_3$.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

APPENDIX A

Poisson Model

To find the maximum of the Poisson model log-likelihood function, we take the derivative of $L^*_P$ with respect to t and set that equal to zero:

$$0 = \sum_i \gamma_i^{(1)}(d_i/\gamma_i - 1) \qquad (10)$$

$$0 = \sum_i \gamma_i^{(2)}(d_i/\gamma_i - 1),$$

where $$\gamma_i^{(1)} = \sum_{j=\tau_{i-1}+1}^{\tau_i} \mu_{1,j}\lambda_j \text{ and } \gamma_i^{(2)} = \sum_{j=\tau_{i-1}+1}^{\tau_i} \mu_{2,j}\lambda_j.$$

The solution to (10), t is our maximum likelihood estimate. To find the necessary terms to estimate $Cov(\hat{t}_i, \hat{t}_j)$ in (4), we take the partial of (10) with respect to $d_i$. For the first equation, we get $$0 = \sum_{j \neq i} \left[ \left( \frac{\partial \gamma_j^{(1)}}{\partial d_i} \right)(d_j/\gamma_j - 1) - \gamma_j^{(1)}(d_j/\gamma_j^2)\left(\frac{\partial \gamma_j}{\partial d_i}\right) \right] + \left[ \left( \frac{\partial \gamma_i^{(1)}}{\partial d_i} \right)(d_i/\gamma_i - 1) + \gamma_i^{(1)}/\gamma_i\left(1 - d_i/\gamma_i\left(\frac{\partial \gamma_j}{\partial d_i}\right)\right) \right]$$

Since we are expanding (3) about $\hat{t}=t$, we can substitute $d_i=\gamma_i$. Also, applying the chain rule, we find $$\frac{\partial \gamma_j}{\partial d_i} = \left(\frac{\partial \hat{t}_1}{\partial d_i}\right)\gamma_j^{(1)} + \left(\frac{\partial \hat{t}_2}{\partial d_i}\right)\gamma_j^{(2)}$$

Substituting these two things, we find:

$$\gamma_i^{(1)}/\gamma_i = \left(\sum_j (\gamma_j^{(1)})^2/\gamma_j\right)\left(\frac{\partial \hat{t}_1}{\partial d_i}\right) + \left(\sum_j (\gamma_j^{(1)}\gamma_j^{(2)})/\gamma_j\right)\left(\frac{\partial \hat{t}_2}{\partial d_i}\right) \quad (10)$$

We arrive at a similar expression from taking the partial of the second equation of (10) with respect to $d_i$. Solving these new expressions for the partial derivatives yields:

$$\begin{bmatrix} \frac{\partial \hat{t}_1}{\partial d_i} \\ \frac{\partial \hat{t}_2}{\partial d_i} \end{bmatrix} = \begin{bmatrix} \sum_j (\gamma_j^{(1)})^2/\gamma_j & \sum_j (\gamma_j^{(1)}\gamma_j^{(2)})/\gamma_j \\ \sum_j (\gamma_j^{(1)}\gamma_j^{(2)})/\gamma_j & \sum_j (\gamma_j^{(2)})^2/\gamma_j \end{bmatrix}^{-1} \begin{bmatrix} \gamma_i^{(1)}/\gamma_i \\ \gamma_i^{(2)}/\gamma_i \end{bmatrix} \quad (11)$$

Since $d_k$ is a Poisson random variable, $\mathrm{Var}(d_k)=\gamma_k$, and we arrive at an expression for $\mathrm{Var}(\hat{t}_1)$, $\mathrm{Var}(\hat{t}_2)$, and $\mathrm{Cov}(\hat{t}_1,\hat{t}_2)$ by substituting (11) into (4).

APPENDIX B

Gaussian Model

We defined $e=E[d]$ and $E$ to be the covariance matrix of $d$. Additionally, define matrix $W$ and vector $w_{(k,1)}$ as $$W=[w_{(1)} \ldots w_{(N)}]$$

$$w_{(k,1)}=[w_{(k),M} w_{(l),M}]^T.$$

Then $e=W^T\lambda$ and $\Sigma_{(i,j)}\lambda$.

To find the maximum, we set the partial of the log-likelihood function with respect to $t$ equal to 0. For the partial with respect to $t_1$, $$0 = \frac{\partial L_G^*}{\partial t_1}$$

$$= -\frac{1}{2}|\Sigma|^{-1}\left(\frac{\partial |\Sigma|}{\partial t_1}\right) - \frac{1}{2}\left[-2\left(\frac{\partial e}{\partial t_1}\right)^T \Sigma^{-1}(d-e) + (d-e)^T\left(\frac{\partial \Sigma^{-1}}{\partial t_1}\right)(d-e)\right]$$

$$= -\frac{1}{2}[tr(\Sigma^{-1}\Sigma^{(1,0)}) - 2e^{(1,0)T}\Sigma^{-1}(d-e) - (d-e)^T\Sigma^{-1}\Sigma^{(1,0)}\Sigma^{-1}(d-e)]$$

where we substituted the following:

$$\frac{\partial |\Sigma|}{\partial t_1} = |\Sigma|tr\left(\Sigma^{-1}\left(\frac{\partial \Sigma}{\partial t_1}\right)\right)$$

$$\frac{\partial \Sigma^{-1}}{\partial t_1} = -\Sigma^{-1}\left(\frac{\partial \Sigma}{\partial t_1}\right)\Sigma^{-1}$$

and defined vector $\lambda^{(k,l)}$ to have elements $\lambda_i^{(k,l)}=(\mu_{1,i})^k (\mu_{2,i})^l \lambda_i$, matrix $\Sigma^{(k,l)}$ to have elements $\Sigma_{ij}^{(k,l)}=w_{(i,j)}^T \lambda^{(k,l)}$, and vector $e^{(k,l)}=W^T\lambda^{(k,l)}$. Then, for instance, matrix $$\frac{\partial \Sigma}{\partial t_1} = \Sigma^{(1,0)}$$

since element $$\left(\frac{\partial \Sigma}{\partial t_1}\right)_{ij} = w_{(i,j)}^T\left(\frac{\partial \lambda}{\partial t_1}\right) = w_{(i,j)}^T \lambda^{(1,0)}.$$

Similarly, we can find the partial of $L^*_G$ with respect to $t_2$. Therefore, the ML estimate, $\hat{t}$, solves the two equations:

$$0 = \quad (12)$$
$$-\frac{1}{2}[tr(\Sigma^{-1}\Sigma^{(1,0)}) - 2e^{(1,0)T}\Sigma^{-1}(d-e) - (d-e)^T\Sigma^{-1}\Sigma^{(1,0)}\Sigma^{-1}(d-e)]$$

$$0 =$$
$$-\frac{1}{2}[tr(\Sigma^{-1}\Sigma^{(0,1)}) - 2e^{(0,1)T}\Sigma^{-1}(d-e) - (d-e)^T\Sigma^{-1}\Sigma^{(0,1)}\Sigma^{-1}(d-e)]$$

To find $$\frac{\partial \hat{t}_1}{\partial d_i},$$

we take the partial of the equations in (12) with respect to $d_i$. For the first equation, $$0 = tr\left(-\Sigma^{-1}\left(\frac{\partial \Sigma}{\partial d_i}\right)\Sigma^{-1}\Sigma^{(1,0)} + \Sigma^{-1}\left(\frac{\partial \Sigma^{(1,0)}}{\partial d_i}\right)\right) -$$
$$2\left[\left(\frac{\partial e^{(1,0)}}{\partial d_i}\right)^T \Sigma^{-1}(d-e) - e^{(1,0)T}\Sigma^{-1}\left(\frac{\partial \Sigma}{\partial d_i}\right)\Sigma^{-1}(d-e) +\right.$$
$$e^{(1,0)}\Sigma^{-1}\left(\delta_i - \left(\frac{\partial e}{\partial d_i}\right)\right)\right] - \left[2\left(\frac{\partial}{\partial d_i}(\Sigma^{-1}(d-e))\right)^T \Sigma^{(1,0)}(\Sigma^{-1}(d-e)) +\right.$$
$$\left.(\Sigma^{-1}(d-e))^T\left(\frac{\partial \Sigma^{(1,0)}}{\partial d_i}\right)(\Sigma^{-1}(d-e))\right]$$

where $\delta_i$ is the unit vector in the i-th dimension. Since we are interested in finding $$\frac{\partial \hat{t}}{\partial d_i}$$

about $d=e$, we can set $d-e=0$. Also, $$\frac{\partial \Sigma^{(k,l)}}{\partial d_i} = \Sigma^{(k+1,l)}\left(\frac{\partial \hat{t}_1}{\partial d_i}\right) + \Sigma^{(k,l+1)}\left(\frac{\partial \hat{t}_2}{\partial d_i}\right)$$

and $$\frac{\partial e^{(k,l)}}{\partial d_i} = e^{(k+1,l)}\left(\frac{\partial \hat{t}_1}{\partial d_i}\right) + e^{(k,l+1)}\left(\frac{\partial \hat{t}_2}{\partial d_i}\right).$$

Hence we get $$0 = tr(\Sigma^{-1}\Sigma^{(2,0)} - (\Sigma^{-1}\Sigma^{(1,0)})^2)\left(\frac{\partial \hat{t}_1}{\partial d_i}\right) +$$

$$tr(\Sigma^{-1}\Sigma^{(1,1)} - \Sigma^{-1}\Sigma^{(0,1)}\Sigma^{-1}\Sigma^{(1,0)})\left(\frac{\partial \hat{t}_2}{\partial d_i}\right) -$$

$$2e^{(1,0)T}\Sigma^{-1}\left[\delta_i - \left(e^{(1,0)}\left(\frac{\partial \hat{t}_1}{\partial d_i}\right) + e^{(0,1)}\left(\frac{\partial \hat{t}_2}{\partial d_i}\right)\right)\right]$$

Combining the results from taking the partial of the second equation in (12) with respect to $d_i$, $$\begin{bmatrix} \frac{\partial \hat{t}_1}{\partial d_i} \\ \frac{\partial \hat{t}_2}{\partial d_i} \end{bmatrix} = \begin{bmatrix} S & R \\ R & T \end{bmatrix}^{-1} \begin{bmatrix} e^{(1,0)T}\Sigma^{-1}\delta_i \\ e^{(0,1)T}\Sigma^{-1}\delta_i \end{bmatrix}$$

$$= \frac{1}{ST-R^2}\begin{bmatrix} T & -R \\ -R & S \end{bmatrix}\begin{bmatrix} e^{(1,0)T}\Sigma^{-1}\delta_i \\ e^{(0,1)T}\Sigma^{-1}\delta_i \end{bmatrix},$$

where $$\begin{bmatrix} S & R \\ R & T \end{bmatrix} = \begin{bmatrix} \frac{1}{2}tr(\Sigma^{-1}\Sigma^{(2,0)} - \Sigma^{-1}\Sigma^{(1,0)}\Sigma^{-1}\Sigma^{(1,0)}) + e^{(1,0)T}\Sigma^{-1}e^{(1,0)} & \frac{1}{2}tr(\Sigma^{-1}\Sigma^{(1,1)} - \Sigma^{-1}\Sigma^{(1,0)}\Sigma^{-1}\Sigma^{(0,1)}) + e^{(1,0)T}\Sigma^{-1}e^{(0,1)} \\ \frac{1}{2}tr(\Sigma^{-1}\Sigma^{(1,1)} - \Sigma^{-1}\Sigma^{(1,0)}\Sigma^{-1}\Sigma^{(0,1)}) + e^{(1,0)T}\Sigma^{-1}e^{(0,1)} & \frac{1}{2}tr(\Sigma^{-1}\Sigma^{(0,2)} - \Sigma^{-1}\Sigma^{(0,1)}\Sigma^{-1}\Sigma^{(0,1)}) + e^{(0,1)T}\Sigma^{-1}e^{(0,1)} \end{bmatrix}$$

Now we can compute the variances and covariance of the ML estimates. Here we compute the variance of estimate $\hat{t}_1$:

$$\mathrm{Var}(\hat{t}_1) \approx \sum_i \sum_j \left(\frac{\partial \hat{t}_1}{\partial d_i}\right)\left(\frac{\partial \hat{t}_1}{\partial d_j}\right)\mathrm{Cov}(d_i, d_j) =$$

$$\left(\frac{1}{ST-R^2}\right)^2 \sum_i \sum_j (Te^{(1,0)T}\Sigma^{-1}\delta_i - R\, e^{(0,1)T}\Sigma^{-1}\delta_i)$$

$$(Te^{(1,0)T}\Sigma^{-1}\delta_j - Re^{(0,1)T}\Sigma^{-1}\delta_j)(w_{(i,j)}^T \lambda) =$$

$$\left(\frac{1}{ST-R^2}\right)^2 \left[T^2 \sum_i \sum_j \Sigma_{ij}(\Sigma^{-1}e^{(1,0)})_i(\Sigma^{-1}e^{(1,0)})_j - \right.$$

$$2TR \sum_i \sum_j \Sigma_{ij}(\Sigma^{-1}e^{(1,0)})_i(\Sigma^{-1}e^{(0,1)})_j +$$

$$\left. R^2 \sum_e \sum_j \Sigma_{ij}(\Sigma^{-1}e^{(0,1)})_i(\Sigma^{-1}e^{(0,1)})_j\right] =$$

$$\left(\frac{1}{ST-R^2}\right)^2 [T^2(e^{(1,0)T}\Sigma^{-1}e^{(1,0)}) - 2TR(e^{(1,0)T}\Sigma^{-1}e^{(0,1)}) +$$

$$R^2(e^{(0,1)T}\Sigma^{-1}e^{(0,1)})].$$

APPENDIX C

Empirical Characteristic Functions

The characteristic function of a distribution is the Fourier transform of its probability density function. For a random variable $r_i$ having a Poisson distribution with mean $\lambda_i$, the characteristic function is $$\phi_{r_i}(s) = E[e^{jsr_i}] \qquad (C.1)$$

$$= \exp(\lambda_i(e^{js} - 1)) \qquad (C.2)$$

where in this section $j=\sqrt{-1}$. The characteristic function has the property that if the random variable $r_i$ is multiplied by a constant $w_i$, then random variable $w_i r_i$ will have a characteristic function $\phi_{w_i r_i}(s) = \phi_{r_i}(w_i s)$. Furthermore, the characteristic function of a sum of independent random variables is equivalent to the product of their characteristic functions. That is, random variable $$d_1 = \sum_{i=1}^{M} w_{1,i} r_i$$

has a characteristic function $$\phi_{d_1}(s) = \prod_{i=1}^{M} \phi_{r_i}(w_{1,i}s) \qquad (C.3)$$

In the case of two weighted measurements, we can also consider the characteristic function of the multivariate random variable $d = (d_1, d_2)$. For $s = (s_1, s_2)$, $$\phi_d(s) = \prod_{i=1}^{M} \phi_{r_i}(w_{1,i}s_1 + w_{2,i}s_2) \qquad (C.4)$$

$$= \exp\left(\sum_{i=1}^{M} \lambda_i(e^{j(w_{1,i}s_1 + w_{2,i}s_2)} - 1)\right)$$

Note that because the characteristic function of a random variable is the Fourier transform of its distribution, $$f(d|t) = \mathcal{F}^{-1}\{\phi_d(s)\} \qquad (C.5)$$

This can be Numerically Computed by Discretizing s and Evaluating $\phi_d(s)$ at these points, giving what is known as the empirical characteristic function. Then, taking the 2D inverse discrete Fourier transform of the empirical characteristic function gives us the empirical distribution of $f(d|t)$. The resolution off depends on the sampled range of s, while the range of f depends on the spacing of the samples of s.

Expanding this method, we can also compute the Fisher matrix exactly.

$$F_{ij}(t) = -E\left[\frac{\partial^2}{\partial t_i \partial t_j}\log f(d|t)\right] \qquad (C.6)$$

$$= E\left[\frac{1}{(f(d|t))^2}\left(\frac{\partial}{\partial t_i}f(d|t)\right)\left(\frac{\partial}{\partial t_j}f(d|t)\right) - \right.$$

-continued $$\frac{1}{f(d\mid t)}\left(\frac{\partial^2}{\partial t_i \partial t_j}f(d\mid t)\right)\Bigg]$$

$$=\int_D \frac{1}{f(x\mid t)}\left(\frac{\partial}{\partial t_i}f(x\mid t)\right)\left(\frac{\partial}{\partial t_j}f(x\mid t)\right) - \left(\frac{\partial^2}{\partial t_i \partial t_j}f(x\mid t)\right)dx$$

where D is the support of d and x is a dummy integration variable. Then the exact CRLB comes from $C_W = F^{-1}$. We have shown that $f(d|t)$ can be found using (C.5), and the other terms in the integral can be numerically computed as well. These terms all contain partial derivative(s), but because the variables d and s are the Fourier transform duals of one another, the partial derivative with respect to t can move inside the Fourier transform. For example, $$\frac{\partial}{\partial t_1}f(d\mid t) = \frac{\partial}{\partial t_1}\mathcal{F}^{-1}\{\phi_d(s)\} \quad \text{(C.7)}$$

$$= \mathcal{F}^{-1}\left\{\frac{\partial}{\partial t_1}\phi_d(s)\right\}$$

$$= \mathcal{F}^{-1}\left\{\left(\sum_{i=1}^{M}\lambda_i^{(1,0)}\left(e^{j(w_{1,i}s_1+w_{2,i}s_2)}-1\right)\right)\cdot\phi_d(s)\right\}$$

and $$\frac{\partial^2}{\partial t_1^2}f(d\mid t) = \mathcal{F}^{-1}\left\{\left(\left(\sum_{i=1}^{M}\lambda_i^{(2,0)}\left(e^{j(w_{1,i}s_1+w_{2,i}s_2)}-1\right)\right) + \left(\sum_{i=1}^{M}\lambda_i^{(1,0)}\left(e^{j(w_{1,i}s_1+w_{2,i}s_2)}-1\right)\right)^2\right)\cdot\phi_d(s)\right\} \quad \text{(C.8)}$$

The other partial derivatives can be similarly computed numerically for any d. Then, because a discretized form of each term in the integrand of (C.6) can be found, the Riemann integral can be found by summing the expression over all samples to arrive at $F_{ij}(t)$.

What is claimed is:

1. A method for determining a composition of an object using a spectral x-ray system, comprising:
   a) transmitting x-ray photons of at least two different energies through the object;
   b) estimating the energy of each detected x-ray photon using a detector in the x-ray system; and
   c) finding a first weighted sum of the number of detected photons of each energy using a first weighting function, wherein the first weighting function is dependent on the attenuation coefficient function of a first material.

2. The method, as recited in claim 1, further comprising finding a second weighted sum of the number of detected photons of each energy using a second weighting function, wherein the second weighting function is dependent on the attenuation coefficient function of a second material different than the first material.

3. The method, as recited in claim 2, further comprising forming an image of the object from the first weighted sum and the second weighted sum.

4. The method, as recited in claim 3, wherein the formed image indicates a composition characteristic of the object.

5. The method, as recited in claim 4, wherein the object comprises a material different than the first material and the second material.

6. The method, as recited in claim 5, wherein the composition of the object is the mass of a material.

7. The method, as recited in claim 6, wherein the first weighting function is proportional to the attenuation coefficient function of the first material.

8. The method, as recited in claim 4, wherein the first material is water.

9. The method, as recited in claim 2, wherein the first weighted sum is $$\int_0^\infty S(E)w_1(E)dE$$

and the second weighted sum is $$\int_0^\infty S(E)w_2(E)dE,$$

wherein $S(E)$ is the number of detected photons of energy E, $w_1(E)$ is the first weighting function, and $w_2(E)$ is the second weighting function.

10. The method, as recited in claim 2, wherein the first weighting function is a linear combination of the attenuation coefficient function of the first material and the attenuation coefficient function of the second material and the second weighting function is a linear combination of the attenuation coefficient function of the first material and the attenuation coefficient function of the second material.

11. The method, as recited in claim 2, further comprising finding a third weighted sum of the number of detected photons of each energy using a third weighting function, wherein the third weighting function is dependent on the attenuation coefficient function of a third material different than the first material and the second material.

12. The method, as recited in claim 2, wherein the first weighting function is proportional to the attenuation coefficient function of the first material.

13. The method, as recited in claim 2, wherein the first material is water.

14. The method, as recited in claim 1, wherein the first weighting function is proportional to the attenuation coefficient function of the first material.

15. A method for determining a composition of an object using a spectral x-ray system, comprising:
   a) transmitting x-ray photons of at least two different energies through the object;
   b) estimating the energy of each detected x-ray photon using a detector in the x-ray system; and
   c) binning each detected x-ray photons according to energy in at least two bins, wherein a gap is between energy thresholds between two bins, wherein photons with energies corresponding to the gap are not counted in any bin.

16. The method, as recited in claim 15, further comprising forming an image of an object from binned detected x-ray photons.

17. An apparatus for determining a composition of an object using a spectral x-ray system, comprising:
   a spectral x-ray source for providing x-ray photons of at least two different energies, placed on a first side of the object;
   a detector for detecting and estimating energies of detected photons on a second side of the object; and a controller, controllably connected to the spectral x-ray source and the detector, comprising:
at least one processor; and
non-transitory computer readable media, comprising:
 computer readable code for controlling the x-ray source to affect transmission of x-ray photons of at least two different energies through the object;
computer readable code for controlling the detector; and
 computer readable code for finding a first weighted sum of the number of detected photons of each energy using a first weighting function, wherein the first weighting function is dependent on the attenuation coefficient function of a first material.

18. The apparatus, as recited in claim 17, wherein the non-transitory computer readable media further comprises computer readable code for determining the composition of the object.

* * * * *